US006620351B2

(12) United States Patent
Gupta et al.

(10) Patent No.: US 6,620,351 B2
(45) Date of Patent: Sep. 16, 2003

(54) METHOD OF FORMING NANOPARTICLES AND MICROPARTICLES OF CONTROLLABLE SIZE USING SUPERCRITICAL FLUIDS WITH ENHANCED MASS TRANSFER

(75) Inventors: Ram B. Gupta, Auburn, AL (US); Pratibhash Chattopadhyay, Auburn, AL (US)

(73) Assignee: Auburn University, Auburn, AL (US)

( * ) Notice: Subject to any disclaimer, the term of this patent is extended or adjusted under 35 U.S.C. 154(b) by 119 days.

(21) Appl. No.: 09/858,301

(22) Filed: May 16, 2001

(65) Prior Publication Data

US 2002/0000681 A1 Jan. 3, 2002

Related U.S. Application Data

(60) Provisional application No. 60/206,644, filed on May 24, 2000.

(51) Int. Cl.[7] .................... B29B 9/00
(52) U.S. Cl. .................... 264/7; 264/9
(58) Field of Search .................... 264/7, 9

(56) References Cited

U.S. PATENT DOCUMENTS 5,043,280 A 8/1991 Fischer et al.
5,301,664 A 4/1994 Sievers et al.
5,360,478 A 11/1994 Krukonis et al.
5,803,966 A 9/1998 Kulshrestha et al.
5,833,891 A 11/1998 Subramaniam et al.
5,864,923 A 2/1999 Rouanet et al.
5,874,029 A 2/1999 Subramaniam et al.
2002/0140118 A1 * 10/2002 Lee .................... 264/9

FOREIGN PATENT DOCUMENTS

EP 0542314 5/1993
WO WO 90/03782 4/1990
WO WO 95/01221 1/1995

OTHER PUBLICATIONS

Sang–Do Yeo et al. "Formation of Microparticulate Protein powders using a supercritical fluid antisolvent", 1993, 341–345.
Luca Benedetti et al. "Production of Micronic Particles of Biocompatible polymer using supercritical carbon dioxide" 1997, 232–236.
Chiehming J. Chang and Alan D. Randolph "Solvent Expansion and Solute Solubility Preditions in gas—expanded liquids", 1990, 939–941.
Pablo G. Debenedetti, "Homogenous Nucleation in Supercritical Fluids", 1990, 1289–1295.

(List continued on next page.)

*Primary Examiner*—Mary Lynn Theisen
(74) *Attorney, Agent, or Firm*—Paul Beck & Associates

(57) ABSTRACT

The current invention, Supercritical Antisolvent Precipitation with Enhanced Mass Transfer (SAS-EM) provides a significantly improved method for the production of nano and micro-particles with a narrow size distribution. The processes of the invention utilize the properties of supercritical fluids and also the principles of virbrational atomization to provide an efficient technique for the effective nanonization or micronization of particles. Like the SAS technique, SAS-EM, also uses a supercritical fluid as the antisolvent, but in the present invention the dispersion jet is deflected by a vibrating surface that atomizes the jet into fine droplets. The vibrating surface also generates a vibrational flow field within the supercritical phase that enhances mass transfer through increased mixing. Sizes of the particles obtained by this technique are easily controlled by changing the vibration intensity of the deflecting surface, which in turn is controlled by adjusting the power input to the vibration source. A major advantage of the SAS-EM technique is that it can be successfully used to obtain nanoparticles of materials that usually yield fibers or large crystals in SAS method. Microencapsulation via coprecipitation of two or more materials can also be achieved using the SAS-EM technique.

29 Claims, 25 Drawing Sheets

OTHER PUBLICATIONS

Theofore W. Randolph et al. "submicrometer–sized biogradeable particle of poly (L–Lactic Acid) via the Gas Antisolvent Spray Precipitation Process", 1993, 429–435.

Ernest Reverchon, "Supercritical antisolvent precipitation of micro and nano particles", 1999, 1–21.

E. Reverchon et al. "Supercritical Antisolvent Precipitation of Nanoparticles of Superconducter Precursors", 1998, pp. 952–958.

Michael A. Winters et al. "Precipitation of Proteins in Supercritical Carbon Dioxide", 1996, 586–593.

Ram B. Gupta, "Ultrasound and a Supercritical Antisolvent based Manufacturing of Nanoparticles"(proposal to the National Science Foundation, Jul. 1998, 3–19.

Ram B. Gupta "Untitled" Resarch Plan to National Institute of Health , Oct. 98, 1–10.

* cited by examiner-

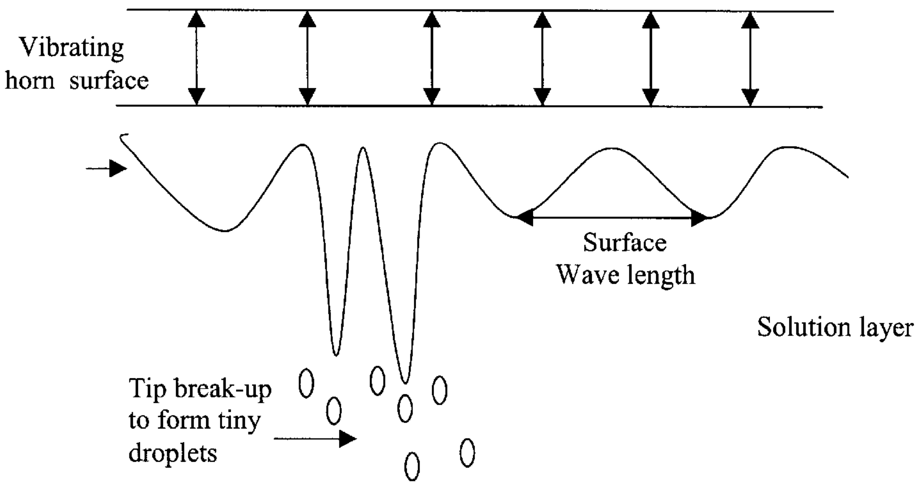
Figure 3. Disintegration mechanism of the liquid film on the horn surface (Drews et al., 1979).

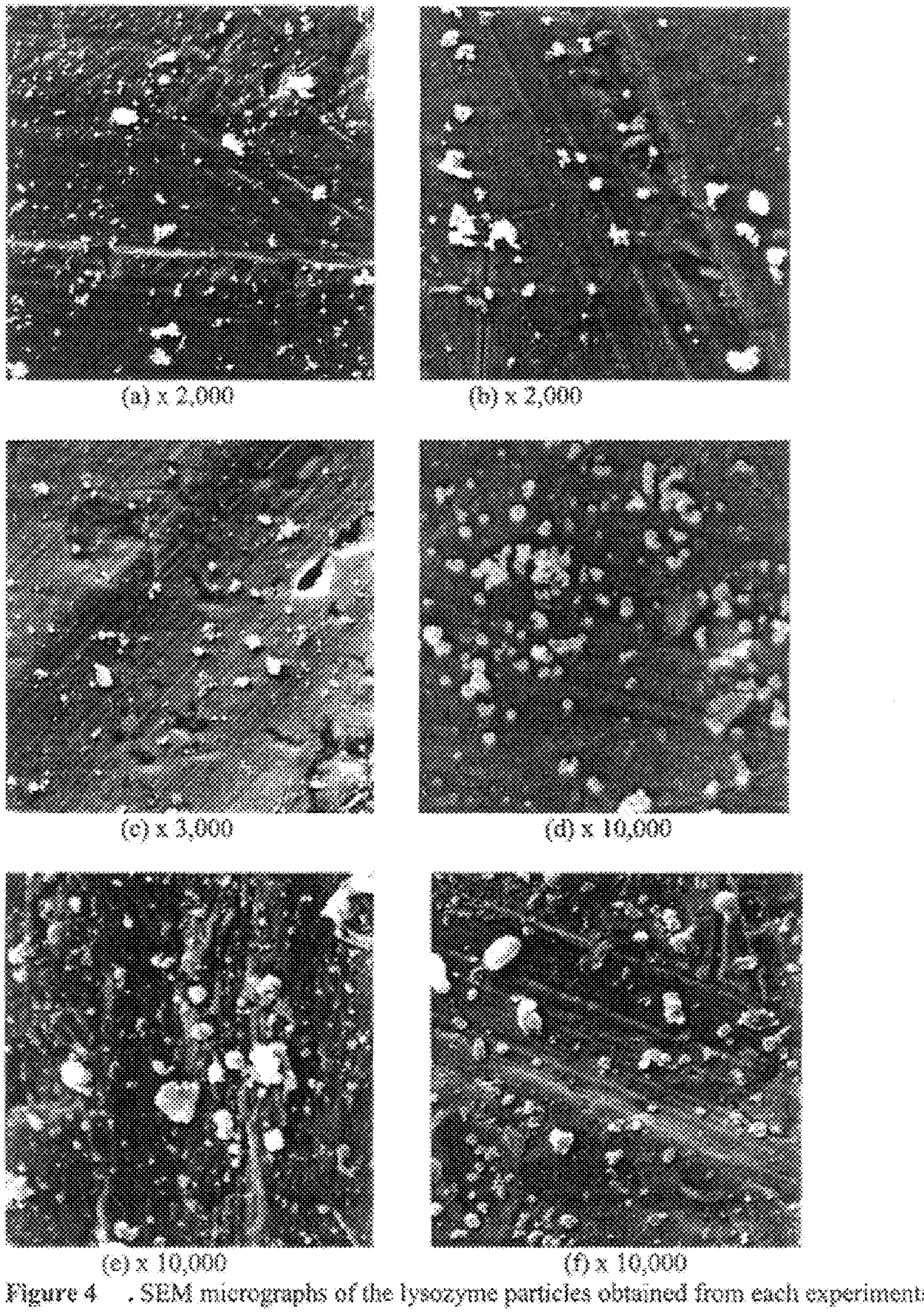
Figure 4 . SEM micrographs of the lysozyme particles obtained from each experiments at different input power to the vibration source at (a) 0 W, (b) 12 W, (c) 30 W, (d) 60 W, (e) 90 W, (f) 120 W power supply. The volume average of particles obtained are (a) 2000 nm, (b) 730 nm, (c) 653 nm, (d) 240 nm, (e) 189 nm, (f) 227 nm.

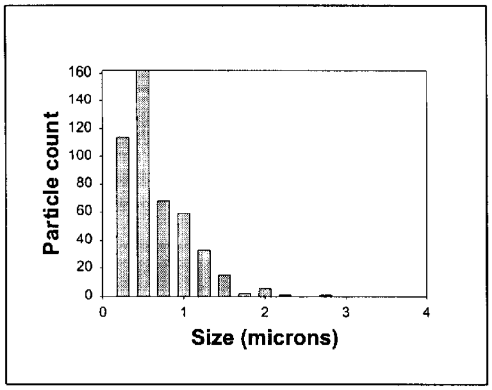
(a) No vibration.
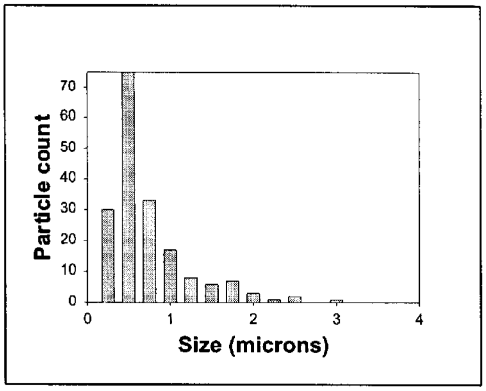
(b) at 12 W power supply.
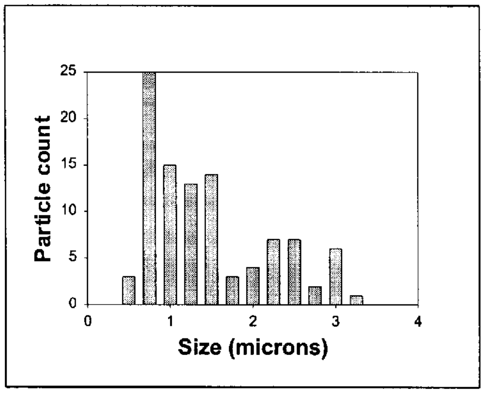
(c) at 30 W power supply.
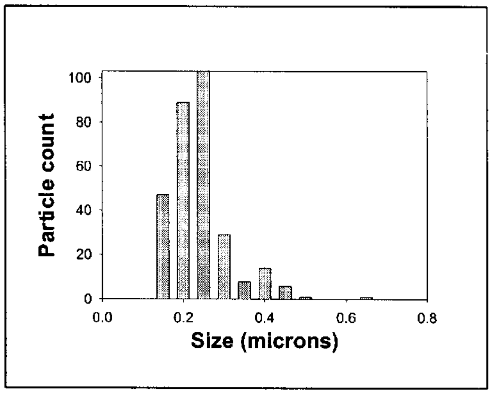
(d) at 60 W power supply.
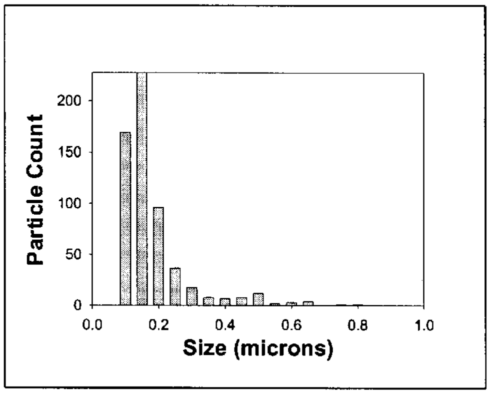
(e) at 90 W power supply.
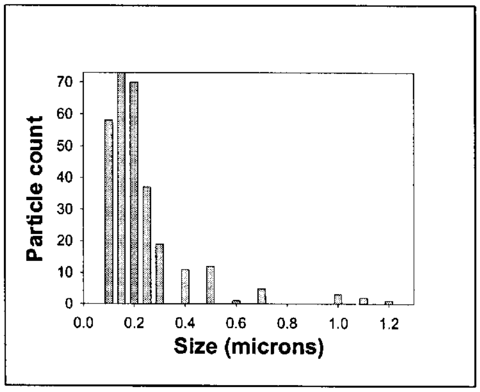
(f) at 120 W power supply.
Figure 5. Particle Size distribution of lysozyme particles obtained from experiments conducted at different input power to the vibration source.

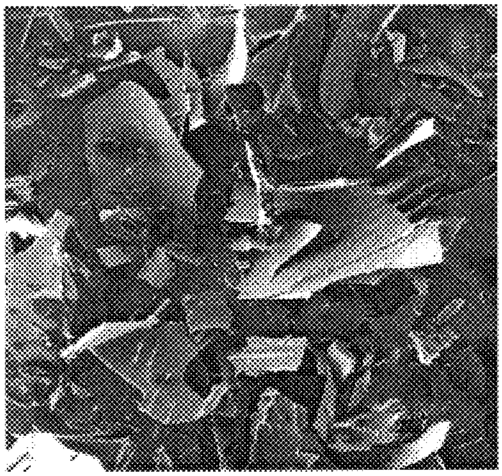
Figure 6. SEM micrograph of untreated lysozyme sample as obtained from the manufacturer. The solid is in the form of flakes a few millimeters in size.

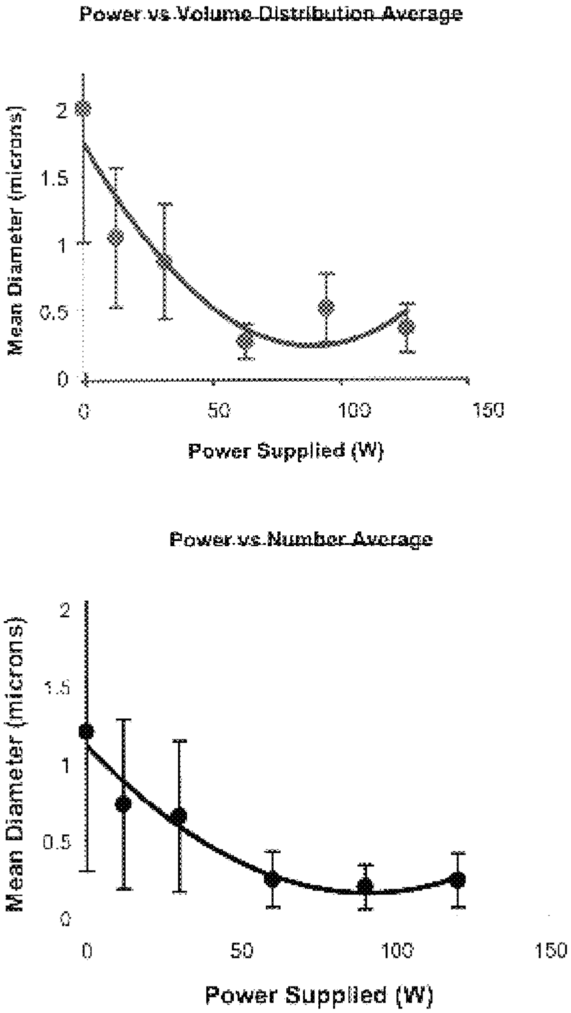
Figure 7. Mean lysozyme particle size versus power supply to the vibration source.

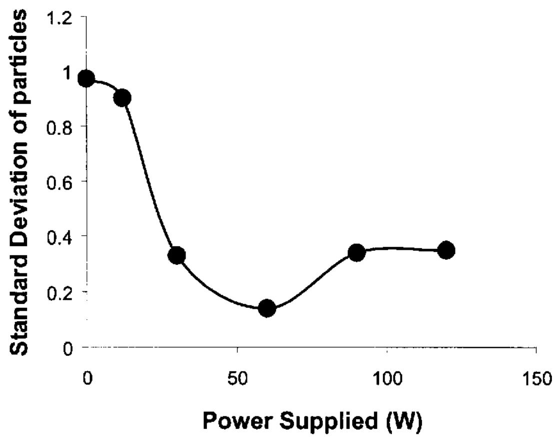
Figure 8. Change in the standard deviation of lysozyme particles with change in the value of the input power supply to the vibration source.

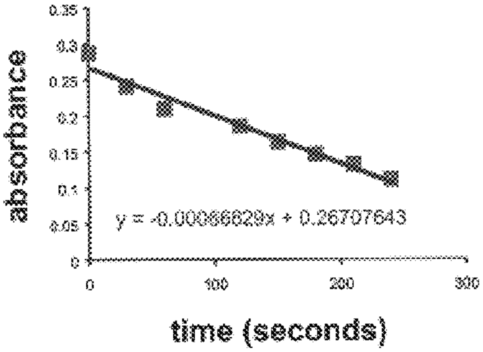
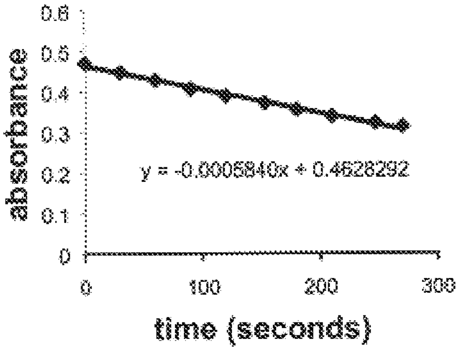
Figure 9. Results of the lysozyme assay tests. Lysozyme supplied by the manufacturer (Top), Lysozyme particles obtained at 96.5 bar, 37°C and at 60 watt input power supply to the vibration source (bottom). Lysozyme particles obtained by the SAS-EM technique retained about 87 % of its activity.

(contd.)
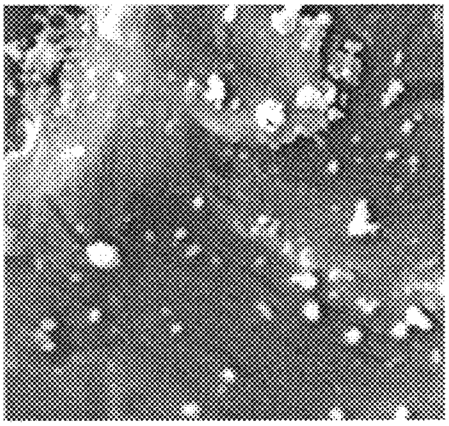
(d1) x 20,000
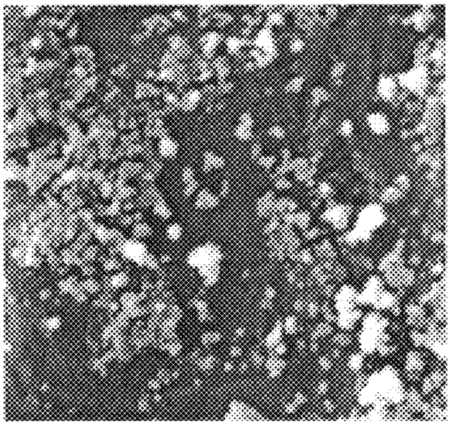
(d2) x 20,000
Figure 10. SEM image of tetracycline particles produced by the SAS-EM process at 96.5 bar, 35 °C, at (a1, a2) 30 W; (b1,b2) at 60 W; (c1, c2) at 90 W and (d1, d2) at 120 W power supply to the vibration source.

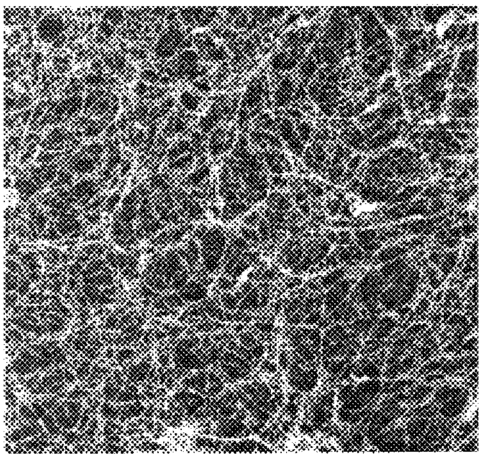
(a) x 1000
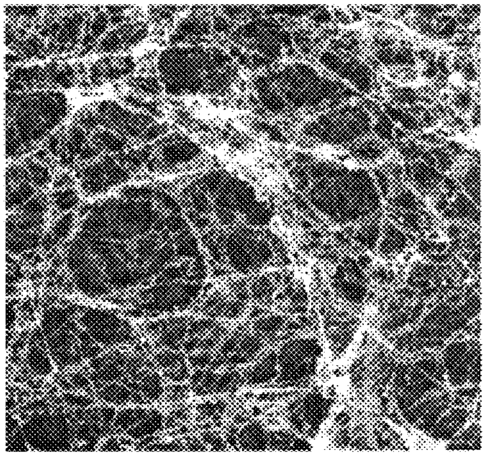
(b) x 2000
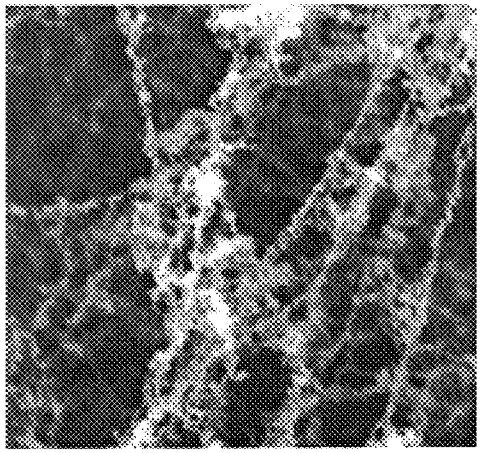
(c) x 10,000
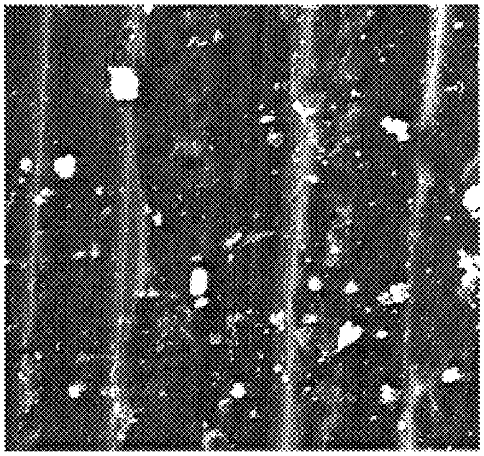
(d) x 2000
Figure 11. SEM image of tetracycline fibers and particles produced by the SAS-EM process at 96.5 bar, 35 °C with no vibration. Most of the solid is in the form of fibers as show in (a-c). A few particles we also obtained as shown in (d).

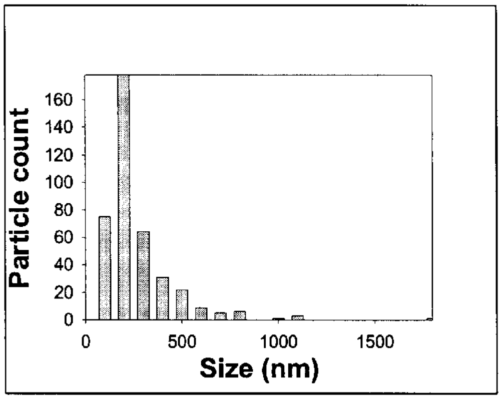
(a) at 30 W power supply.
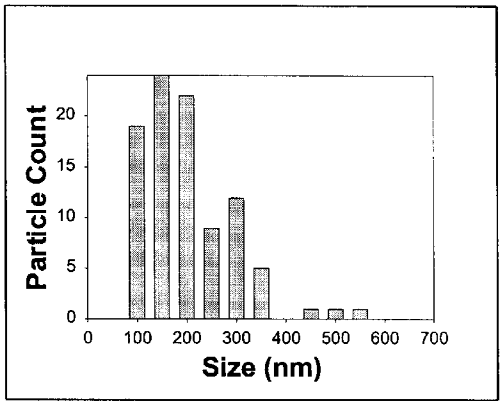
(b) at 60 W power supply.
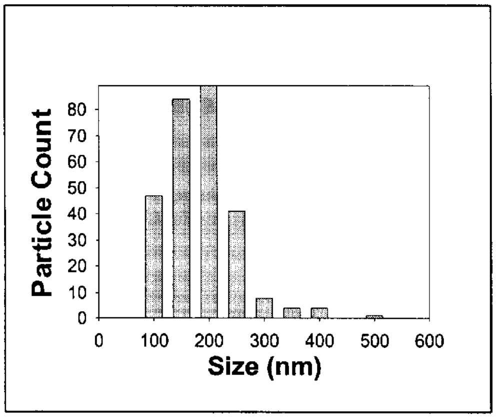
(c) at 90 W power supply.
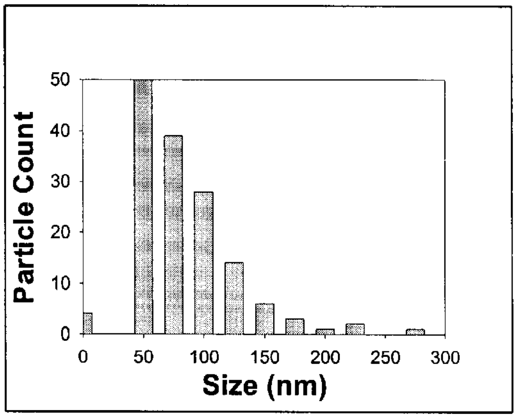
(d) at 120 W power supply.
Figure 12. Size distribution of lysozyme particles obtained from experiments conducted at varying input powers to the vibration source.

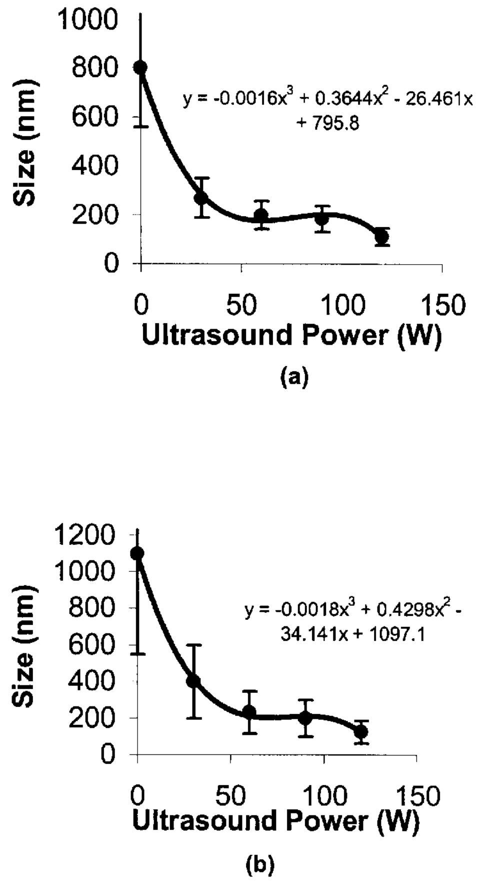
Figure 13. Average tetracycline particle sizes versus power supply to the vibration source: (a) number average, and (b) volume average

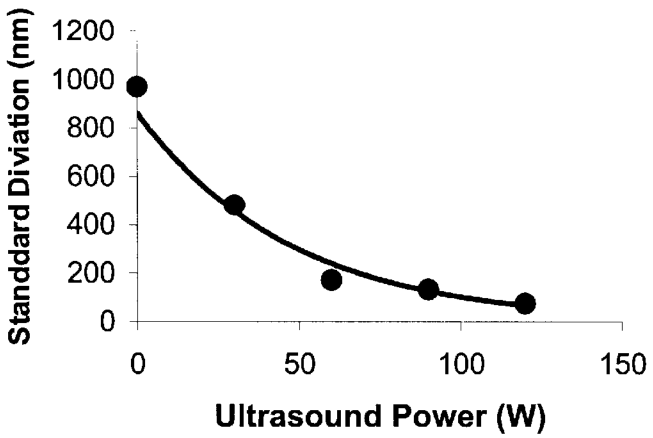
Figure 14. Standard deviation in the size of the lysozyme particles versus power supplied to the vibration source.

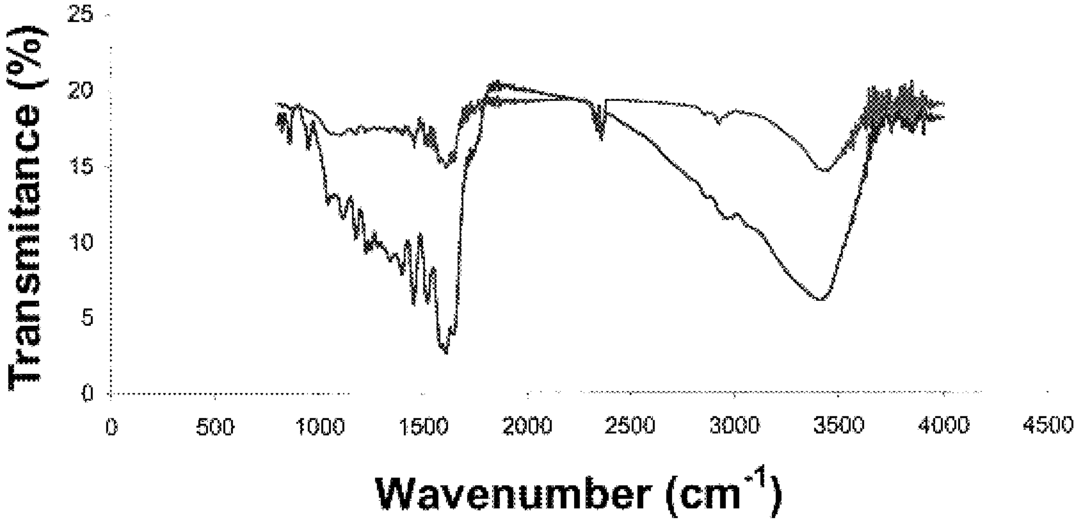
Figure 15. IR spectra of tetracycline as obtained from the manufacturer and the after processing with SAS-EM technique

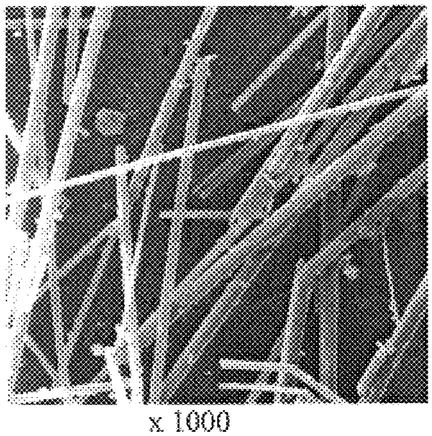
x 1000
(a) No Power supply.
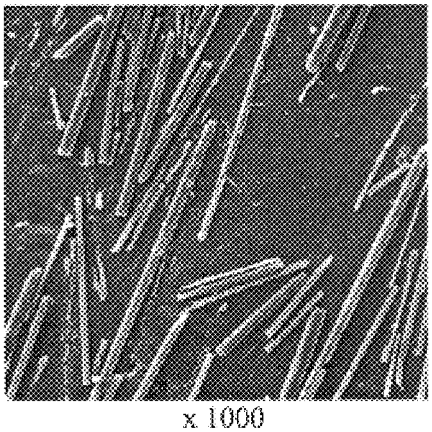
x 1000
(b) 60 W power supply
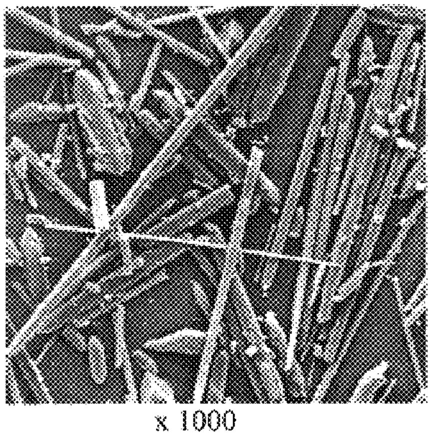
x 1000
(c) 90 W power supply
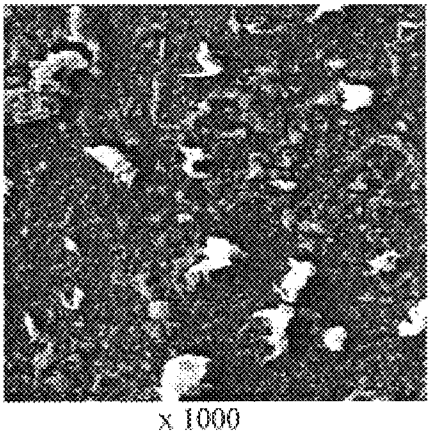
x 1000
(d) 120 W power supply
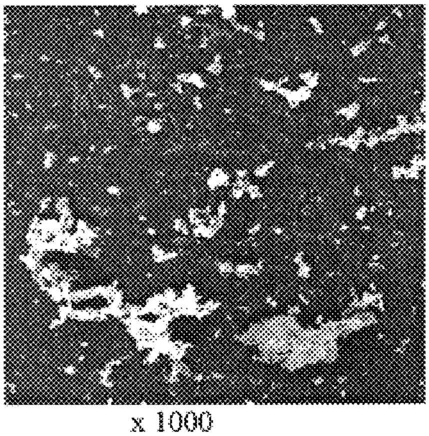
x 1000
(e) 150 W power supply
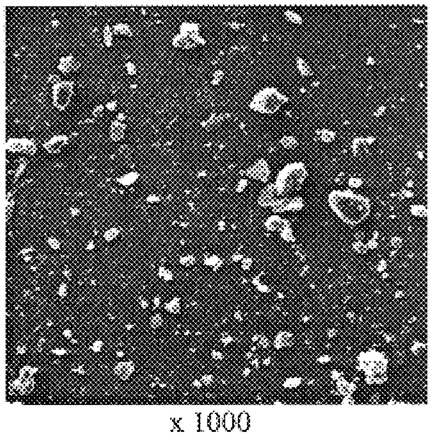
x 1000
(f) 180 W power supply
Figure 16. SEM micrographs showing the change in the morphologies of Griseofulvin particles obtained from experiments conducted at different values of power supply to the vibration source using DCM as solvent.

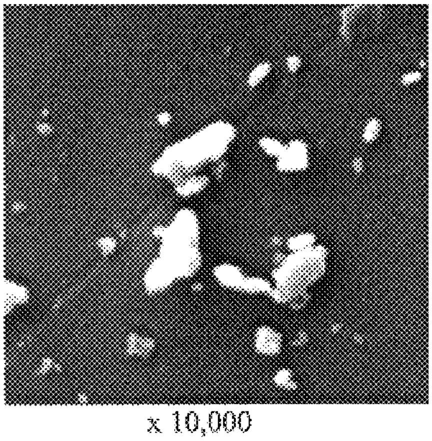
x 10,000
(a) 90 W power supply.
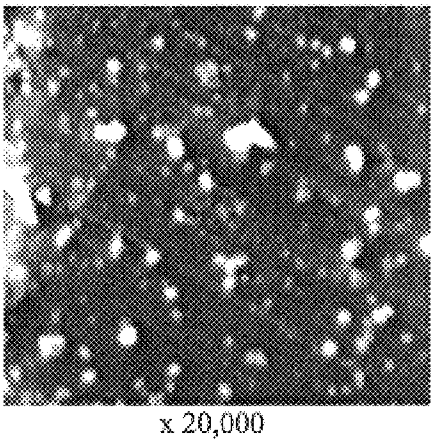
x 20,000
(b) 120 W power supply
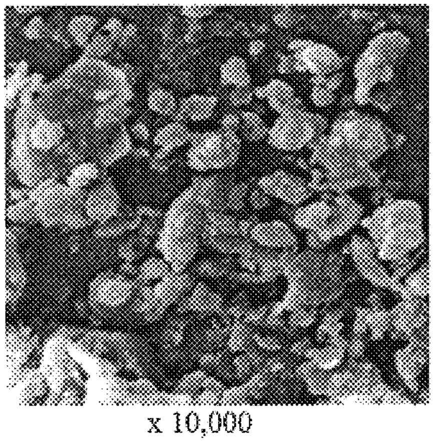
x 10,000
(a) 150 W power supply.
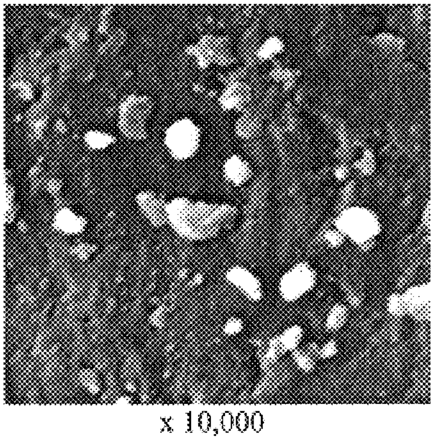
x 10,000
(b) 180 W power supply.
Figure 17. SEM micrographs of spherical shaped Griseofulvin nanoparticles obtained from experiments conducted at different values of power supply to the vibration source using DCM as solvent.

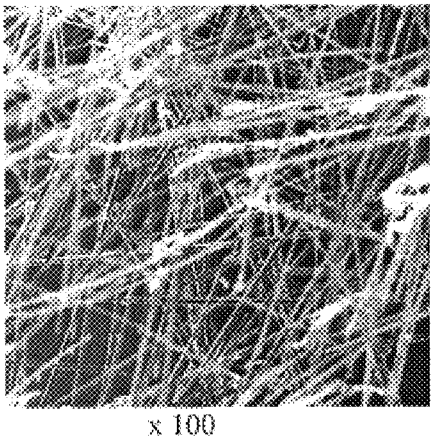
x 100
(a) No power supply.
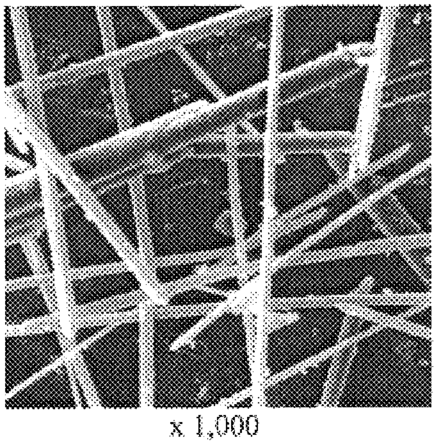
x 1,000
(b) 90 W power supply
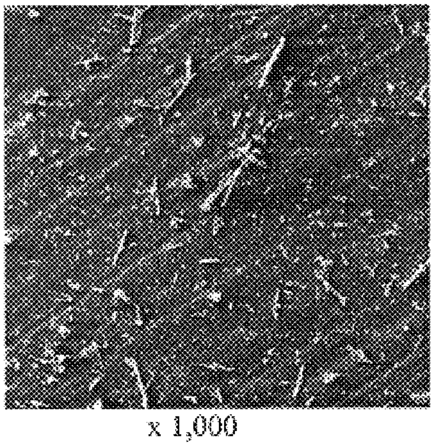
x 1,000
(a) 120 W power supply.
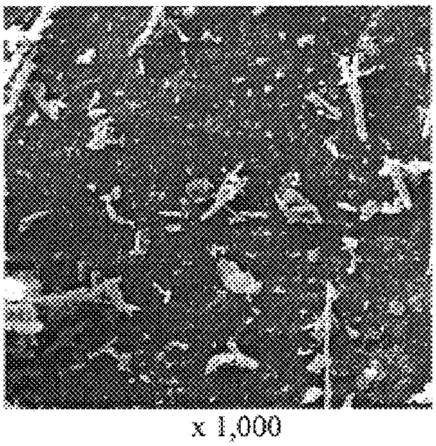
x 1,000
(b) 150 W power supply
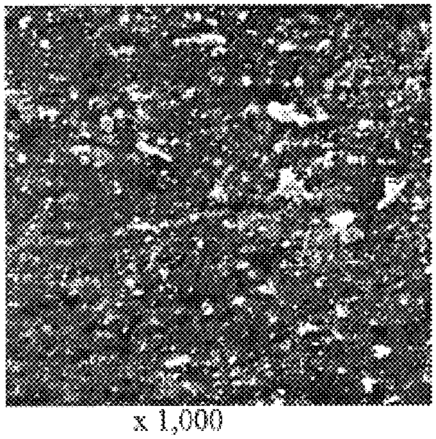
x 1,000
(a) 180 W power supply.
Figure 18. SEM micrographs showing the change in the morphologies of Griseofulvin particles obtained from experiments conducted at different values of input power supply using THF as solvent.

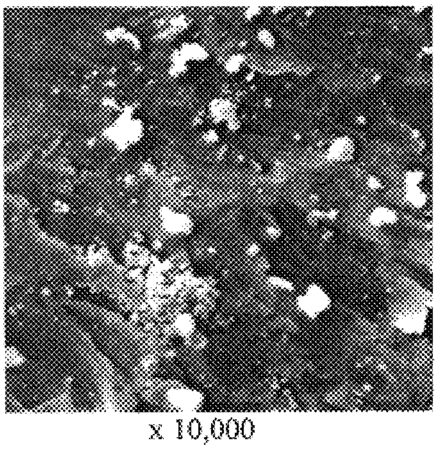
x 10,000
(a) 120 W power supply.
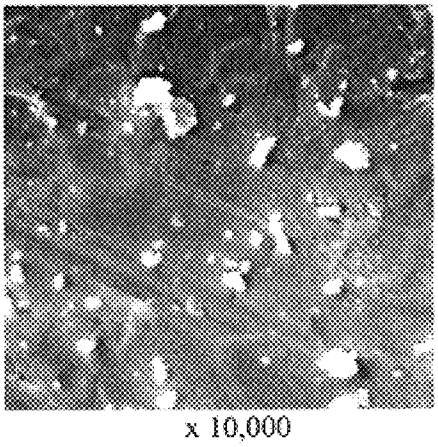
x 10,000
(b) 150 W power supply
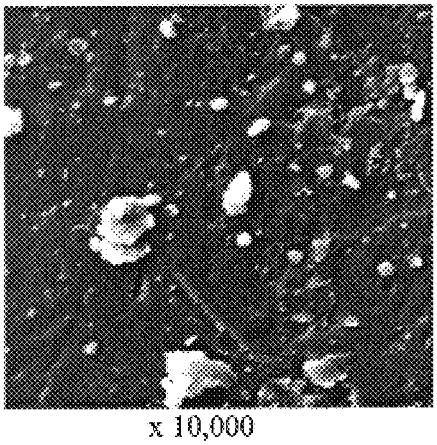
x 10,000
(a) 180 W power supply.
Figure 19. SEM micrographs of spherical shaped Griseofulvin nanoparticles obtained from experiments conducted at different values of input power supply, using THF as solvent.

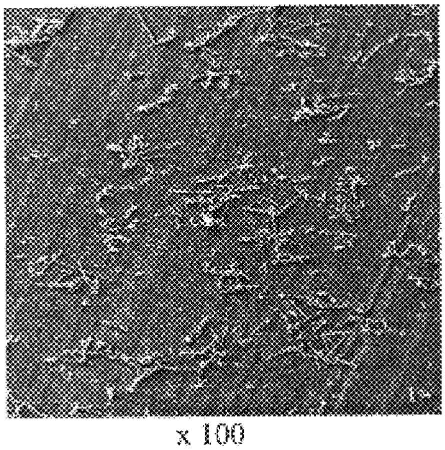
x 100
(a) 60 W power supply
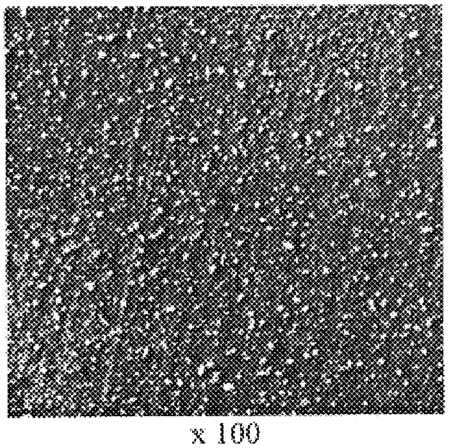
x 100
(b) 120 W power supply.
Figure 20. SEM micrographs illustrating the change in the morphology of the Griseofulvin particles with increasing value of input power supply to the vibration source using DCM as solvent.

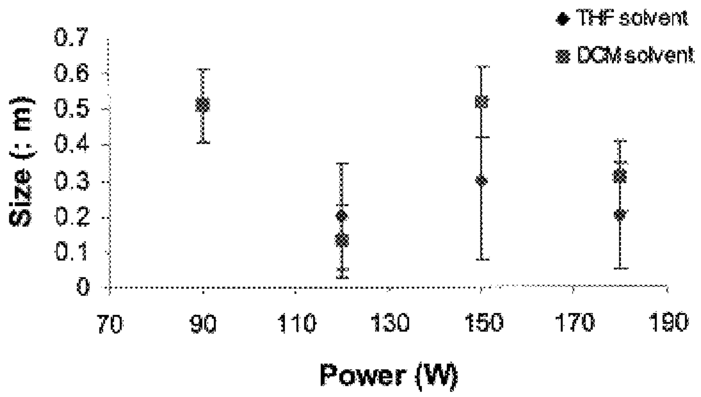
Figure 21. Volumetric mean size of spherical shaped Griseofulvin obtained particles vs the input power supply to the vibration source.

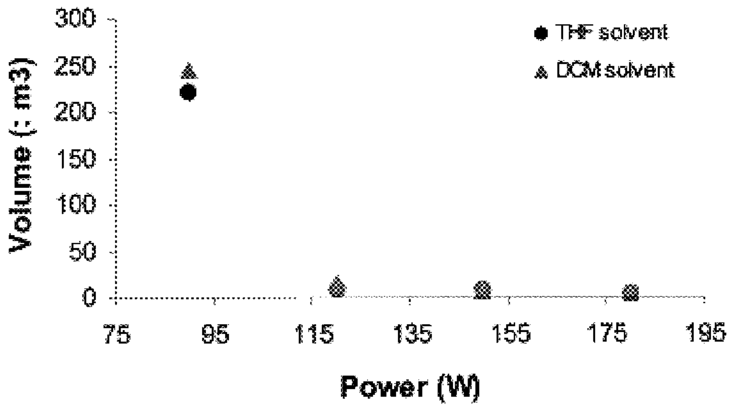
Figure 22. Volume of long needle shaped Griseofulvin crystals obtained vs the input power supply to the vibration source.

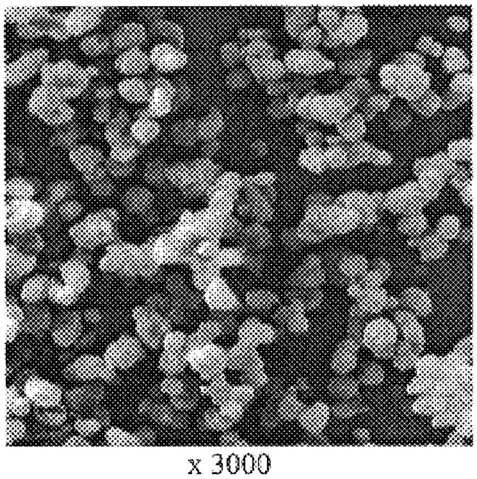
x 3000
No vibration used
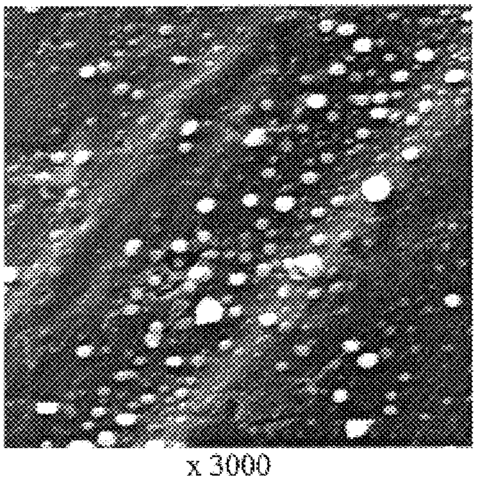
x 3000
60W power supply
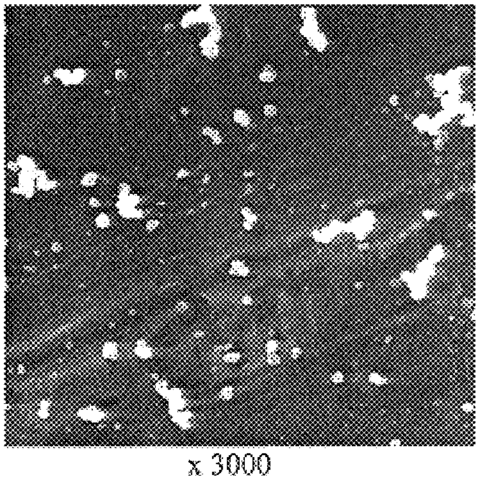
x 3000
120 W power supply
Figure 23. SEM micrographs of spherical shaped polymer encapsulated magnetite nanoparticles obtained from experiments conducted at different values of input power supply to the vibration source, using DCM as solvent.

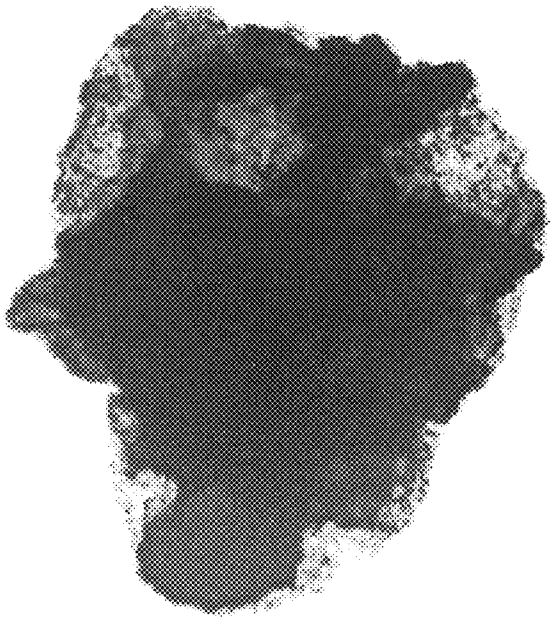
Figure 24. TEM micrograph of PLGA encapsulated magnetite particle. The dark and shady regions are due to the magnetite particles inside PLGA.

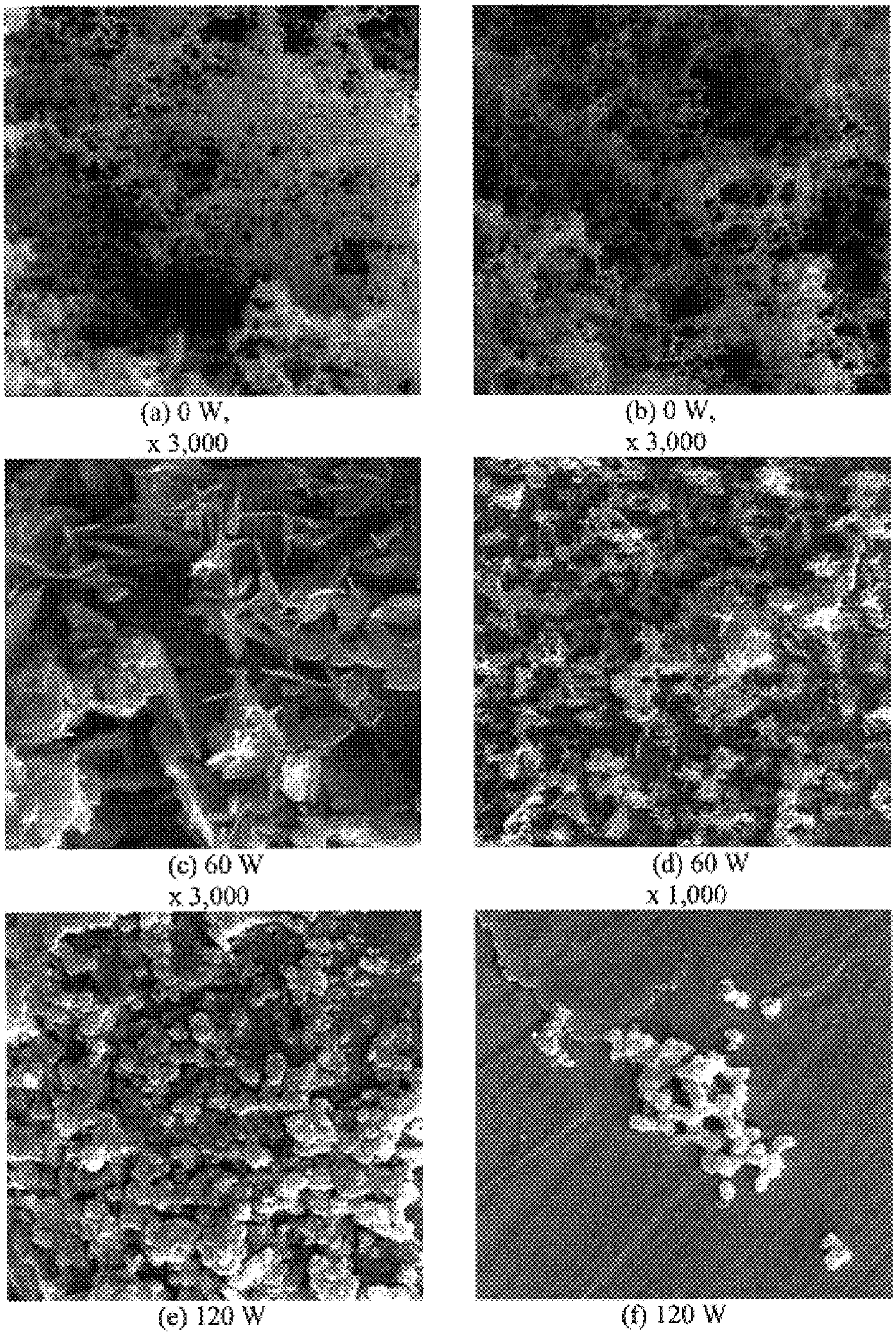
(a) 0 W,
x 3,000
(b) 0 W,
x 3,000
(c) 60 W
x 3,000
(d) 60 W
x 1,000
(e) 120 W
x 20,000
(f) 120 W
x 10,000
Figure 25. SEM micrographs of tetracycline particles obtained using the SAS-EM technique at 96.5 bar, 35 °C and at a vibration frequency of 20 kHz. The nozzle used in this case was a 760 im stainless steel tube.

METHOD OF FORMING NANOPARTICLES AND MICROPARTICLES OF CONTROLLABLE SIZE USING SUPERCRITICAL FLUIDS WITH ENHANCED MASS TRANSFER

CROSS-REFERENCE TO RELATED APPLICATION

This application claims benefit from the Provisional patent application Serial No. 60/206,644 filed on May 24, 2000 and entitled METHOD OF FORMING NANOPARTICLES AND MICROPARTICLES OF CONTROLLABLE SIZE USING SUPERCRITICAL FLUIDS AND ULTRASOUND, teachings of which are incorporated herein by reference.

FEDERALLY SPONSORED APPLICATION

The U.S. Government has a paid-up license in this invention and the right in limited circumstances to require the patent owner to license others on reasonable terms as provided for by the terms of Grant No. CTS-9801067 awarded by the National Science Foundation Grant and Grant No. 1-R55-RR13398-01 awarded by the National Institute of Health.

BACKGROUND OF THE INVENTION

1. Field of Invention

The current invention relates to a method for the production of micron or nanometer size particles by precipitation, wherein a dispersion containing the substance of interest is contacted with a supercritical fluid antisolvent under near or supercritical conditions in order to maximize micro or nanoparticle formation. The invention also provides techniques to control the particle size, particle size distribution and particle morphology. The invention also includes supercritical fluid coating or composite material particle formation, wherein encapsulation of one substance by another substance or coprecipitation of more than one substance in the form of micro or nanoparticles are achieved in the supercritical fluid antisolvent.

2. Background and Prior Art

Nanoparticles are of considerable importance in numerous technological applications. Nanoparticles of materials in fact exhibit properties significantly different from those of the same material with larger sizes. Some nanostructured materials with novel properties include: fullerenes, zeolites, organic crystals, non-linear optical material, high temperature superconductors, molecular magnetic materials, starburst dendrimers, piezoelectric materials, shape changing alloys and pharmaceuticals. The novel properties of these nanostructured materials can be exploited and numerous potential applications can be developed by using them in different industries. One such industry where the need for nanoparticles is particularly pronounced is the pharmaceutical industry where nanoparticles of different pharmaceutical materials are used for designing ‘drug delivery systems’ for controlled release and targeting.

Several techniques have been used in the past for the manufacture of nanoparticles but these techniques suffer from some inherent limitations. Some of the conventional techniques include: Spray drying, which is one of the well-known techniques for particle formation and can be used to produce particles of 5 $\mu$m or less in size. The major disadvantage of this technique is that it requires high temperature in order to evaporate the solvent in use, and this makes it unsuitable for treating biological and pharmaceutical substances. Furthermore, the final product yield may be low in case of small-scale applications. Milling can be used to produce particles in the 10–50 $\mu$m range, but the particles produced by this method have a broad size distribution. Fluid energy grinding can produce particles in the 1–10 $\mu$m range but this process involves the use of high-velocity compressed air, which leads to electrostatically charged powders. In addition, particle size reduction by this process tends to be more efficient for hard and brittle materials such as salt and minerals, but much less so for soft powders, such as pharmaceuticals and other biological substances. Lyophilization produces particles in the desired range, but with a broad distribution. A main disadvantage of this process is that it employs the use of organic solvents that may be unsuitable for pharmaceutical substances. In addition, control of particle size can also be difficult, and a secondary drying step is required to remove residual solvents. In the case of precipitation of protein particles, not all proteins can be lyophilized to stable products, and the process must be tailored to each protein.

Thus, none of these methods are entirely satisfactory, and it is therefore important to explore alternative methods that will produce particles from 5 $\mu$m down to as low as 10 nm.

Particle Technology Based on Supercritical Fluids

One of the first uses of supercritical fluids in particle formation was proposed by Krukonis et al. in 1984 for processing a wide variety of difficult-to-handle solids. Since then, several experimental studies have been conducted to develop methods for particle formation using this technology. The two primary methods utilizing supercritical fluid technology for particle processing include Supercritical Antisolvent (SAS) Precipitation technique and the Rapid Expansion of Supercritical Solutions (RESS) technique. For many years now, these techniques have been successfully used to produce microparticles of various compounds including difficult to handle explosives (Gallagher et al., 1989), lysozyme, trypsin (Winter et al, 1993), insulin (Yeo et al., 1993; Winter et al, 1993), prednisolone acetate (U.S. Pat. No. 5,803,966), polystyrene (Dixon et al., 1993), HYAFF-11 polymers (Benedetti et al., 1997), different steroids (Larson and King, 1985), and numerous other organic substances. Other areas of application of supercritical fluids include formation of solvent free, drug loaded polymer micro-spheres for controlled drug release of therapeutic agents (Tom et al., 1992; Mueller and Fischer, 1989), production of ultra-fine and chemically pure ceramic precursors (Matson et al., 1985 a,b, 1987 a,b; Peterson et al. 1985), formation of intimate mixtures of ceramic precursors (Matson et al., 1987a), and for formulation of crystalline powders of labile pharmaceutical drugs. Dixon and coworkers (1993) used the supercritical $CO_2$ antisolvent process to make polystyrene particles ranging from 0.1 to 20 $\mu$m by spraying polymer/toluene solutions into $CO_2$ of varying densities. A major advantage of supercritical fluid precipitation process is that they can generate particles having a narrow size distribution unlike other conventional processes that provide a wide size distribution. Further the particles formed by supercritical fluid precipitation process are free of organic solvents and the formation of powdered blends, thin films and micro-encapsulation of materials is straightforward.

The Working of the RESS Technique

In the RESS process, the solid of interest is first solubilized in supercritical $CO_2$ and then sprayed through a nozzle into a low-pressure gaseous medium. Rapid expansion of the solution on being passed through the nozzle causes a reduction in $CO_2$ density and also a reduction in the solvent power of supercritical $CO_2$ and this subsequently leads to the recrystallization of the solid in the form of fine particles.

RESS provides a useful tool for controlling the size and morphology of the precipitated powders. The influence of operating conditions on the process has been studied by several investigators, sometimes with different and conflicting results (Larson and King, 1985; Mohamed et al., 1989; Peterson et al., 1985). When RESS is carried out in the usual mode, solvent free particles are obtained which makes the technique advantageous for processing pharmaceutical substances. No surfactants or nucleating media are required to trigger the nucleation and the solvent is removed by a simple mechanical separation.

One of the main constraints in the development of the RESS process however is supercritical fluid solvent capacity. For example, carbon dioxide, which is the preferred solvent in many applications, has a low solubility towards polar substances. Different supercritical fluids can be chosen in case of such a problem: a second solvent (cosolvent) can be added to enhance the $CO_2$ solvent capacity, but these solvents remains within the precipitated product as impurities. In general, polymers possess low solubility in supercritical fluids, including $CO_2$ (with or without cosolvents), and for such materials other processing methods are more suitable.

The Working of the SAS Process

In the SAS process, the supercritical fluid is used as the antisolvent. First the solid of interest is dissolved in a suitable organic solvent. Then this solution is introduced into the supercritical fluid using a nozzle. The supercritical fluid dissolves the solvent, precipitating the solid out as fine particles.

The volumetric expansion of the liquid when in contact with the SCF plays a key role in the process. For example, experiments conducted by Yeo et al. (1993a,b) for dimethylsulfoxide (DMSO)-$CO_2$ system at two temperatures, shows that $CO_2$ produces a remarkably high volumetric expansion of DMSO (as high as 1000%) near the mixture's critical point. The increase of antisolvent amount in the mixed solvent and the evaporation of the organic liquid into the SCF eventually cause the precipitation of the solute as fine particles.

Several methods of applying the SAS technique have also been proposed. In the semibatch mode, the SCF is introduced continuously at the operating pressure into a stationary bulk liquid phase (Gallagher et al., 1989; Krukonis, 1988). If the liquid solution and the SCF are fed continuously to the precipitation tank, a SAS continuous process takes place (Yeo et al., 1993a,b). When the solvent used has a high volatility, it is possible to continuously feed the solution and the supercritical fluid into the precipitation vessel and, at the same time to discharge the dry precipitated particles (Randolph et al., 1993). Finally, a full batch mode is performed where the solution is loaded with the supercritical solvent from the initial condition at P=1 atm. to the high pressure (Yeo et al., 1993a,b).

Note that, in all cases, a cleaning step is necessary after the precipitation step in order to completely remove the liquid solvent from the particles. One of the interesting features of SAS is that the particles may be dried with $CO_2$, and the $CO_2$ may be depressurized at supercritical fluid conditions. Supercritical fluid drying removes the solvent thoroughly, which is often a major challenge. When liquids are evaporated from a matrix, the surface tension of the shrinking droplets often causes the matrix to collapse due to capillary forces. For a supercritical fluid, there is no surface tension, and the surface forces due to adsorption are minimal, so that the structure is preserved. Indeed the world's lightest solids have been formed with critical point drying (Rangarajan and Lira, 1991).

Current Limitations of the SAS Process

The SAS technique can be used to produce particles having a narrow size distribution in the 1–10 μm size range. Unfortunately these techniques cannot produce much smaller particles in the nanometer range. Nanometer size particles are extremely important for many pharmaceutical applications. New applications of nanoparticles of other substances can also emerge if the nanoparticles are manufactured successfully. In any SAS technology, mass transfer rate of the antisolvent into the droplet is the key factor in obtaining a high super-saturation rate and a smaller particle size, and hence mass transfer is the limiting factor in the SAS process. Techniques that can enhance mass transfer and provide faster diffusion of $CO_2$ into the droplets are thus needed for the formation of smaller particles having a narrower size distribution. Operating temperature, pressure, concentration of the injecting solution, and flow rate of the solution have so far been investigated as size control parameters but none of these parameters were found to have a significant effect on the particle size over a wide range.

In the past few years several modifications (mostly in the manner of jet break up) in the SAS process have been proposed in order to overcome some of its limitations. For example in PCT publication WO 95/01221 the use of a coaxial nozzle for co-introduction of supercritical fluid and the solution has been proposed. Such nozzles cause effective breakup or atomization of the solution jet into tiny droplets. But, again a rigorous size control process variable is lacking. The use of high frequency sound waves for atomization has been known for many years for the atomization of liquid surfaces into tiny droplets. High frequency sound waves can be generated using various types of transducers namely piezoelectric, magnetorestrictive, electromagnetic, and pneumatic devices.

A specialized ultrasonic nozzle (Sonotek, 120 khz) was employed by Randolph et al. (1993) in the precipitation of poly (L-lactic acid) particles using the SAS technique. But they were unsuccessful in reducing the particle size as a result of the use of ultrasound. U.S. Pat. Nos. 5,833,891 and 5,874,029 disclose the use of ultrasound in small particle production. They disclose the use of a commercial ultrasonic nozzle (Sonomist, Model 600-1) for the droplet atomization. The sonic waves in this case are created when an energizing gas passes through a resonator cavity at the velocity of sound. The frequency of the sonic waves created is not constant and it is difficult to specify the frequency of the sound waves generated. Trying to vary the sonic energy might interfere with other process conditions and as a result it may not be used as a size control variable.

SUMMARY OF THE INVENTION

The Supercritical Antisolvent Precipitation with Enhanced Mass Transfer (SAS-EM) Process The present invention provides a novel way to produce very small particles in the nanometer range, having a narrow size distribution. It also provides techniques to control the particle size. The processes and methods involved in the invention can be used for producing nanoparticles of a wide variety of materials such as polymers, chemicals, pesticides, explosives, coatings, catalysts and pharmaceuticals. Like the SAS technique, the current invention also uses a supercritical fluid as the antisolvent, but in this invention the dispersion jet is deflected by a vibrating surface that atomizes the jet into micro-droplets. The dispersion jet once introduced into supercritical fluid and onto the vibrating surface spreads evenly over the surface forming a thin liquid film. A set of wavelets then form on the free liquid layer due to the vibrating surface. The oscillatory vibrations of the liquid surface causes these wavelets to increase in amplitude until the wavelet tips break off and the droplets are emitted from the surface into the supercritical fluid media. Rapid transfer of $CO_2$ into these droplets and the solvent out of these droplets causes them to expand rapidly, leading to a decrease in the droplet's ability to keep the solute molecules dissolved causing the molecules to precipitate as fine particles. The vibration field generated by the vibrating surface inside the supercritical phase helps in enhancing mass transfer between the solvent and the supercritical fluid due to increased turbulence and mixing. The reduced mean droplet diameter coupled with enhanced turbulence within the supercritical phase cause rapid precipitation of the particles and thus act as major factors that are responsible for the formation of nanoparticles.

The present invention uses high frequency vibrations for atomization. The atomization process is brought about by introducing the dispersion on to a surface vibrating at a high frequency. No specialized nozzles are necessary in this invention. Any tube made of a standard material (for example: Stainless Steel, Fused Silica) can be used to spray the dispersion onto the horn surface. The diameter of the tube can be varied based on the desired size and desired yield of the micronized particles.

A schematic representation of the apparatus used for particles processing using the SAS-EM technique in the batch mode has been shown in FIG. 1. All the particle precipitation runs can be carried out using the methods in the invention either in the batch mode or in the semibatch mode. The first step, as in any antisolvent precipitation technique involving supercritical fluids, is filling up the particle production vessel with the antisolvent. This is done up to the desired operating pressure which is typically around or above the critical pressure of the antisolvent. Any antisolvent can be used including carbon dioxide, propane, butane, isobutene, nitrous oxide, sulfur hexafluoride and trifluoromethane, but carbon dioxide is the most preferred antisolvent due to its low cost, environmental friendliness and the ease of availability. The temperature inside the vessel is maintained constant at the desired value by placing the vessel in a temperature controlled zone. The temperature is typically above or around the critical temperature of the antisolvent. Dispersion containing desired substance is prepared. The horn inside the vessel is then turned on to vibrate at the desired amplitude by adjusting the input power to the vibrating source. The horn in fact provides the vibrating surface inside the supercritical phase for both dispersion jet atomization and increased mixing. The dispersion is then injected inside the precipitation chamber through a silica capillary tube, onto the vibrating surface. It is important to note here that tubes having different diameters can be used to carry out the precipitation process but in our case a 75 $\mu$m (internal diameter) capillary tube was used. As the dispersion jet makes contact with the vibrating horn surface, it is atomized into tiny droplets and particles are formed due to the rapid removal of the solvent by supercritical $CO_2$ from these droplets. Motion between the particles inside the chamber is increased due to the vibration field generated by the vibration surface, which in turn prevents them from agglomerating together and also increases the mass transfer rate of $CO_2$ into the droplet, and the solvent out of the droplet.

In one preferred embodiment of the current invention the precipitation or recrystallization process using SAS-EM is carried out in a continuous manner. In this form of the invention the supercritical fluid is preheated and pumped into the vessel in a continuous manner at a desired flow rate. A preheated dispersion, having at least one solid of interest dissolved in at least one suitable solvent, is then injected into the vessel and onto the vibrating surface inside the precipitation vessel in a continuous manner at a desired flow rate. $CO_2$ flow rate is kept high enough to completely dry the particles and remove all solvents.

A major advantage of the present invention over other forms of supercritical fluid particle precipitation techniques is that the sizes of the particles formed by this technique can be easily controlled by changing the vibration intensity of the deflecting surface, which in turn can be controlled by adjusting the input power to the vibrating source. For instance the size control parameters investigated so far in the SAS process are pressure and temperature of the antisolvent, concentration of the dispersion and the flow rate of the dispersion into the supercritical fluid antisolvent. All these parameters are not robust enough to generate a pronounced change in particle size. Besides, conflicting results have been obtained by different researchers about the actual effect of these parameters on particle size and distribution and no general trend has been established.

Another major advantage of the present invention is that it can be used to produce nanoparticles of compounds that cannot be obtained using the SAS method. In other words compounds that give long fibers or large crystals using the SAS technique can be processed using the SAS-EM technique to form nanoparticles or microparticles.

One of the main requirements of such small particles in several applications is a narrow particle size distribution. SAS-EM can be used to produce particles with narrow size distributions as a result of uniform droplet atomization.

In another preferred embodiment of the current invention encapsulation of one substance can be achieved using another substance to form coated nanoparticles. The core particle to be coated is dispersed in a suitable medium and mixed with a dispersion containing the desired substance and sprayed on to the deflecting surface in the vessel to obtain very small particles coated with the desired substance. Change in vibration intensity is used to decrease the particle size of such coated or encapsulated particles. Composite nanoparticles of two or more substances can also be obtained using the preferred embodiments of the current invention. In this aspect of the invention, the dispersion for injection is prepared by dissolving the substances to be co-precipitated in a suitable solvent or a mixture of solvents. Surfactants may also be employed for dispersing some substances in the suitable medium or solvent. The above dispersion is then sprayed onto the deflecting vibrating surface for atomization and production of particles. For example the co precipitation can be used to produce drug loaded polymer nanoparticles or magnetite encapsulated polymer nanoparticles that can be used for controlled release and drug targeting.

BRIEF DESCRIPTION OF THE DRAWINGS

FIG. 3 is a representation of the mechanism for the liquid film disintegration on the horn surface.

FIG. 4 is SEM micrographs of the particles obtained from each experiments at (a) 0 W, (b) 12 W, (c) 30 W, (d) 60 W, (e) 90 W, (f) 120 W power supply to the horn. The volume average of particles obtained are (a) 2000 nm, (b) 730 nm, (c) 653 nm, (d) 240 nm, (e) 189 nm, (f) 227 nm.

FIG. 5 is a representation of particle size distribution of lysozyme particles obtained from experiments conducted at different horn input powers.

FIG. 6 is an SEM micrograph of untreated lysozyme sample as obtained from the manufacturer. The solid is in the form of flakes a few millimeters in size.

FIG. 7 is a representation of mean lysozyme particle size versus power supply to the horn.

FIG. 8 is a representation of change in the standard deviation of lysozyme particles with change in the value of the total power supply to the horn.

FIG. 9 is the results of the lysozyme assay tests. Lysozyme supplied by the manufacturer (Top), Lysozyme particles obtained at 96.5 bar, 37° C. and at 60 watt power supply (bottom). Lysozyme particles obtained by the SAS-EM technique retained about 87% of its activity.

FIG. 10 is SEM micrographs of tetracycline particles produced by the SAS-EM process at 96.5 bar, 35° C., at (a1, a2) 30 W; (b1, b2) at 60 W; (c1, c2) at 90 W and (d1, d2) at 120 W power supply.

FIG. 11 is SEM micrographs of tetracycline fibers and particles produced by the SAS-EM process at 96.5 bar, 35° C. with no vibration. Most of the solid is in the form of fibers as shown in (a–c). A few particles were also obtained as shown in (d).

FIG. 12 is a representation of the size distribution of lysozyme particles obtained from experiments conducted at varying input powers.

FIG. 13 is a representation of average tetracycline particle sizes versus power supply to the horn: (a) number average, and (b) volume average.

FIG. 14 is a representation of standard deviation in the size of the lysozyme particles versus power supplied to the vibrating horn.

FIG. 15 is the IR spectra of tetracycline as obtained from the manufacturer and after processing with SAS-EM technique.

FIG. 16 is SEM micrographs showing the change in the morphologies of Griseofulvin particles obtained from experiments conducted at different input power supply to the vibrating source, using DCM as solvent.

FIG. 17 is SEM micrographs of spherical shaped Griseofulvin nanoparticles obtained from experiments conducted at different input power supply, using DCM solvent.

FIG. 18 is SEM micrographs showing the change in the morphologies of Griseofulvin particles obtained from experiments conducted at different values of input power supply, using THF solvent.

FIG. 19 is SEM micrographs of spherical shaped Griseofulvin nanoparticles obtained from experiments conducted at different values of input power supply, using THF solvent.

FIG. 20 is SEM micrographs illustrating the change in the morphology of the Griseofulvin particles with increasing power supply to the horn using DCM as solvent.

FIG. 21 is a representation of volumetric mean size of spherical shaped Griseofulvin obtained particles versus power supply.

FIG. 22 is a representation of volume of long needle shaped Griseofulvin crystals obtained versus power supply.

FIG. 23 is SEM micrographs of spherical shaped polymer encapsulated magnetite nanoparticles obtained from experiments conducted at different input power, using DCM as solvent.

FIG. 24 is a TEM micrograph of PLGA encapsulated magnetite particles. The dark and shady regions are due to magnetite particles inside PLGA.

FIG. 25. SEM micrographs of tetracycline particles obtained using the SAS-EM technique at 96.5 bar, 35° C. and at a vibration frequency of 20 kHz. The nozzle used in this case was a 760 μm stainless steel tube.

DETAILED DESCRIPTION OF THE INVENTION

Definitions

"Particles" means

Figure 1:
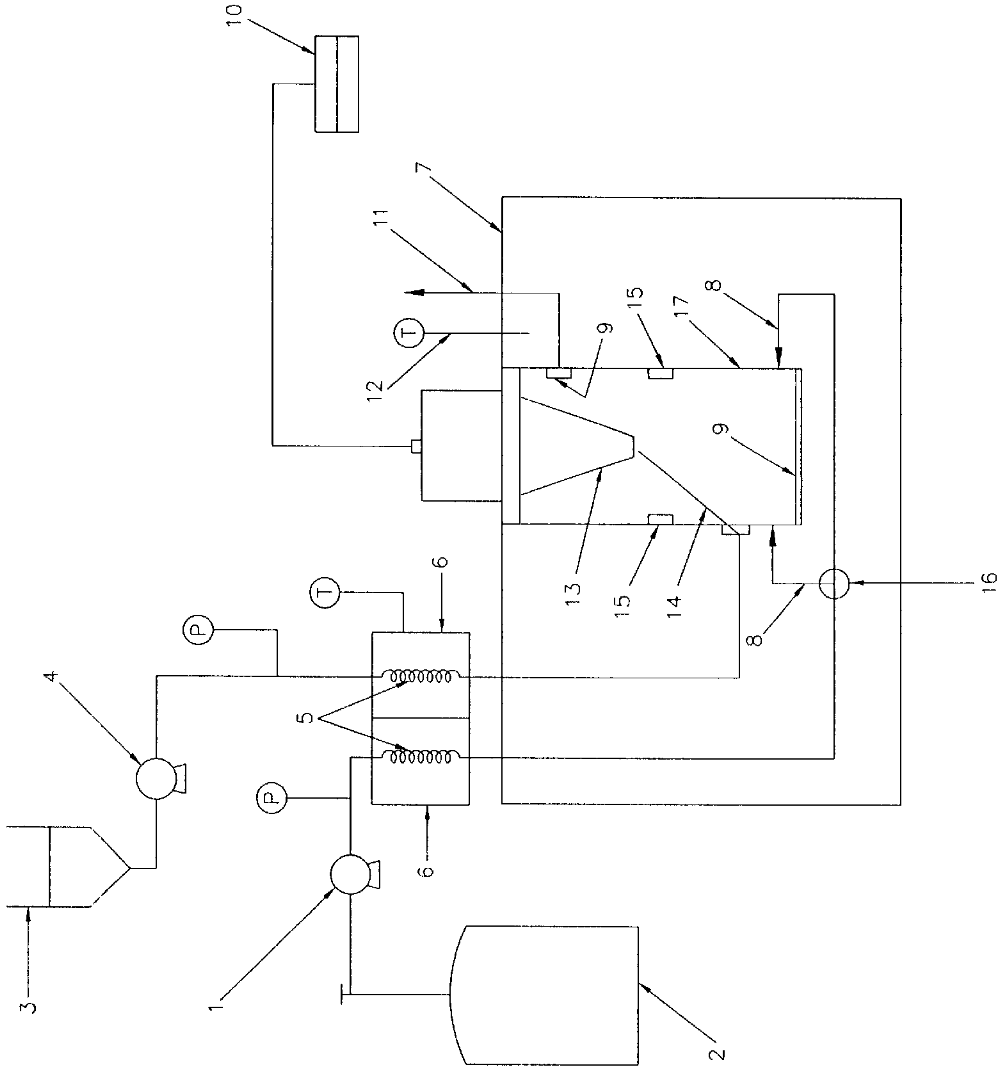
FIG. 1 is a schematic representation of the apparatus employed for particle production using the SAS-EM technique.
Figure 2:
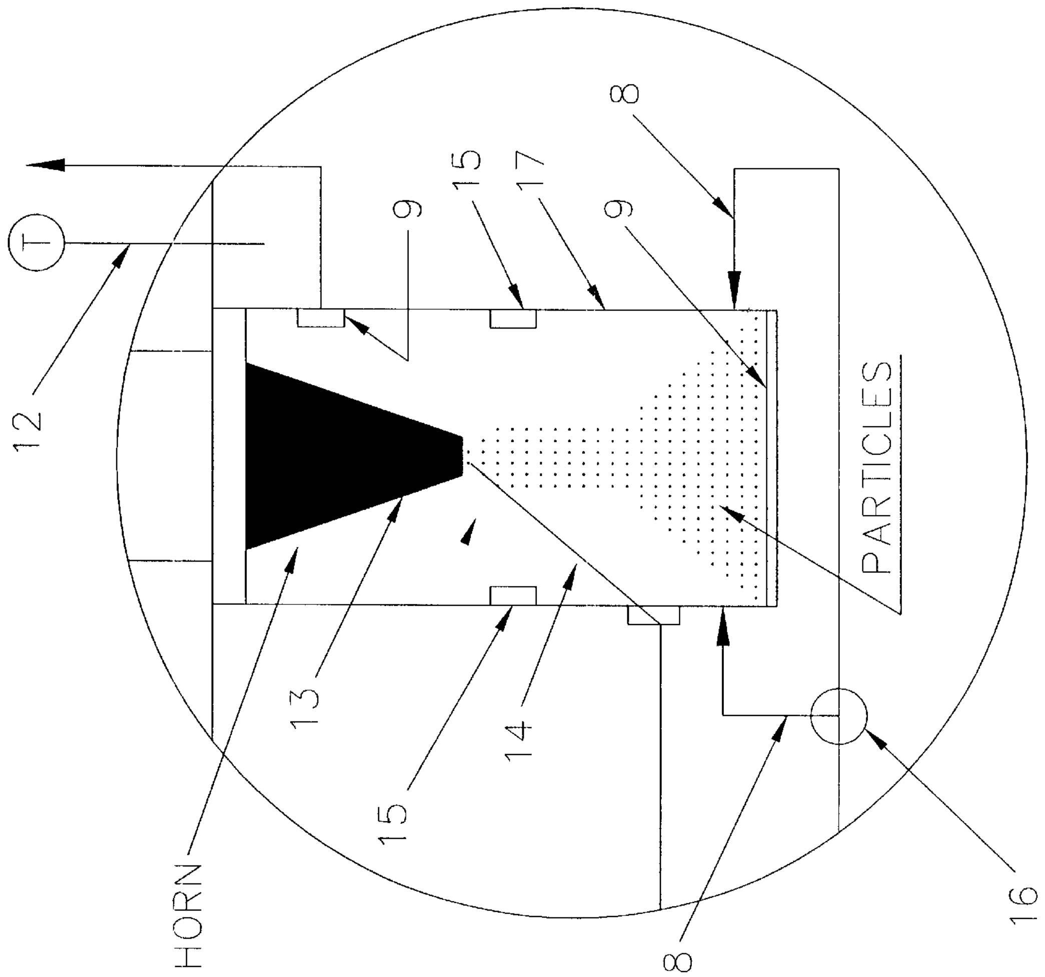
FIG. 2 is a schematic representation of the particle production vessel.

A particle is a relatively small discrete portion of a given material.

"Desired substance" means

The material comprising of one or more substances of interest.

"Dispersant" means a fluid that helps in dispersing or scattering a material in a medium.

"Dispersion" means

A homogenous or a heterogeneous mixture of the desired substance in one or more suitable solvents with or without dispersants or coreparticles.

"Solvent" means

A fluid or a combination of fluids, which can dissolve the desired substance in order to form a homogenous solution.

"Surface" means

The exterior or the boundary of the horn tip excluding any nozzle surface onto which the dispersion is sprayed.

"Vibrating the surface" means

Moving the surface at a rapid rate by means of an external source.

"Desired frequency" means a frequency being from 0.5 khz to 1 Mhz, preferably from 10 khz to 200 khz.

"Antisolvent" means a fluid that does not substantially dissolve a desired substance.

"Near or supercritical conditions" means the temperature and pressure of the fluid being closer to or higher than the critical temperature and critical pressure of the fluid respectively. Preferably, the temperature being from 0.7 $T_c$ (K) to 1.5 $T_c$ (K) and pressure being from 0.2 $P_c$ to 10 $P_c$.

"Miscible" means two substance being soluble in each other.

"Substantially Insoluble in the antisolvent" means the desired substance has no or very little solubility in the antisolvent.

"Droplets" means

A relatively small drop that can exist independently in the supercritical fluid medium.

"Supercritical fluid" means

A fluid whose temperature and pressure are kept above its critical temperature and pressure respectively.

"Size of the particles" means

The dimensions of the precipitated particles. Typically, it is the diameter of the particle if it is fairly spherical and the length and the width if the particle is in the form of a rod or a needle.

"Distribution of the particles" means the distribution of the particle counts for different particle sizes.

"Intensity of the vibration" means

The degree of vibration or the extent to which the surface vibrates. It is directly proportional to the input power to the vibrating source. Higher the intensity of vibration greater is the amplitude of vibrating the surface.

"Piezoelectric" means

A material capable of generating vibrations when subjected to applied voltage.

"Magnetorestrictive" means

A material capable of generating vibrations when subjected to a change in its state of magnetization.

"Agglomeration of the particles" means

The particles being clustered together to form a larger mesh or a sphere like structure.

"Collecting the particles in a continuous manner" means

Collection of the produced particles in a manner that does not require stopping the production of particles "Coreparticles" means particles that are to be coated or surrounded by the desired substance.

"Encapsulated coreparticles" means coreparticles being surrounded or coated by the desired substance.

"Medicaments" means substances used in the diagnosis, treatment, or prevention of disease and for restoring, correcting, or modifying organic functions.

"Morphology of the particle" means external structural appearance or the form of the particle.

"close to the vibrating surface" means close to the vibrating surface so as to get exposed to at least one wavelength of vibration. Typically one wavelength of vibration with 20 Khz frequency in the vessel is about 2 cm.

Description

The current form of the invention can be practiced either in a batch mode, or in a continuous manner for particle collection. FIG. 1 is a schematic of the apparatus used in particle production using SAS-EM. Pump 1 is used to pump $CO_2$ at a constant pressure and at a desired flow rate. Similarly, pump 4 is used to flow the dispersion at a constant pressure and desired flow rate. Both streams are pumped through individual temperature controlled zones to maintain a desired inlet temperature into the particle production vessel 17. The $CO_2$ inlets are located close to the bottom of the vessel and the flow rates in the individual inlets can be controlled by a control valve 16. The dispersion 3 is sprayed through a dispersion inlet 14 at an angle between 0 to 90 degrees to the horn surface 13. The horn surface 13 is vibrated through either piezoelectric or magnetorestrictive means. The transducer 10 allows to control the intensity or input energy to the vibration source which in turn controls the amplitudes of vibration. The vessel is kept in a temperature controlled zone 7 and $CO_2$ outlet 11 is located at the top of the vessel and $CO_2$ is further taken for recycle. The windows 15 are used for visual inspection and for online particle measurements. Temperature and pressure sensors are employed accordingly at various locations. The following steps explain the preferred embodiments of the practice of the current invention.

The particle production vessel 17 is filled with the antisolvent up to the desired operating pressure (near or above the critical pressure of the antisolvent) and maintained at the desired operating temperature (near and above the critical temperature of the antisolvent). The antisolvent from source 2 is pumped through a temperature controlled zone 6 and let into the vessel 17 in a continuous manner at a desired flow rate.

The horn surface 13 inside the vessel 17 is then vibrated at the desired amplitude by adjusting the input power to the transducer 10. The frequency of vibration is generally kept at a constant 20 Khz. Vibration can also be produced with magnetorestrictive, electromagnetic or pneumatic means. This horn provides the surface 13 on to which the dispersion jet is injected for atomization. The change in amplitude results in decreased droplet size which eventually translates to smaller precipitated particles.

The dispersion 3 containing one or more substances of interest in one or more suitable solvents is pumped through the temperature controlled zone 6 in order to control the inlet temperature and sprayed through the dispersion inlet 14. The distance between the outlet of the dispersion inlet 14 and the horn surface 13 is kept small and can be varied to prevent clogging of the dispersion inlet 14 tip.

As soon as the dispersion 3 jet is in contact with the vibrating surface, it is atomized into tiny droplets and particles are formed due to the rapid removal of the solvent/solvents by supercritical $CO_2$ from the droplets. The mass transfer rate between solvent/solvents and supercritical $CO_2$ is greatly enhanced due to increased mixing caused by the vibration field generated by the horn surface 13. Increased mixing also leads to an increase in particle motion inside the precipitation vessel 17 and this further prevents agglomeration of the precipitated particles.

The vibration field generated by the horn surface 13 causes vibration streaming inside the particle production vessel 17, which keeps the particles in constant motion.

The flow rate of $CO_2$ is maintained high enough so that all the solvents in the dispersion 3 are removed to obtain dry particles.

Dry particles are collected in a particle barrier 9. This collection can be made continuous by moving the collection zone away from the precipitation zone.

The particle morphology is also controlled by the change in input power intensity to the vibration source. This changes the amplitude of vibrations of the horn surface. Change in intensity also produces narrower particle size distribution.

Various aspects of the current invention and its salient features have been demonstrated by the following examples, which set forth techniques, process parameters, operating conditions and also a list of the obtained experimental results. Test results to prove that no structural or biological change in the precipitated compounds took place as a result of the precipitation process have also been listed. Examples 1–3 relate to the precipitation of pharmaceuticals such as lysozyme, tetracycline and Griseofulvin (GF). Example 4 illustrates the precipitation of fullerene nanoparticles. Potential applications of these nanoparticles can be envisioned once their unique physical and chemical properties have been determined after their manufacture. Example 5 relates to coating of a coreparticle with one or more desired substances. The coreparticles are dispersed in the chosen solvent with use of a surfactant and this mixture is mixed with a solution containing the desired substance. The resultant dispersion is injected onto the deflecting surface inside the particle production vessel 17. In the example, polymer encapsulated magnetite particles have been produced using the methods of the current invention.

(1) Formation of Lysozyme Particles

The SAS-EM technique was applied to the formation of lysozyme particles of different sizes, using the power supplied to the horn as the size tuning parameter. The particle production vessel was kept constant at 96.5 bar and 37° C. and the frequency of the horn vibrations was maintained at 20 kHz. The solution containing lysozyme in dimethyl sulfoxide (DMSO) (concentration 5 mg/ml) was introduced into the vessel at different horn vibration amplitudes corresponding to 0–120 W input power supply. As soon as the solution was injected lysozyme particles were formed inside the vessel which were then collected and taken for analysis.

FIGS. 4*a–f* show scanning electron (SEM) micrographs of particles obtained in experiments conducted at the different vibration amplitudes.

With no vibration (i.e., when the input power/amplitude is zero) the volume distribution mean size of particle is around 2 μm with standard deviation of 1 μm. It is important to note here that the experiment conducted at zero amplitude is the same as the conventional SAS technique and the nozzle in this case was kept parallel to the horn surface 13. In SAS-EM experiments, nozzle is placed at angle to the horn surface 13 (0–90°) to maximize the solution jet exposure to the horn surface 13. As the horn amplitude values are increased, there is a considerable decrease in particle size to as low as 0.26 μm at the amplitude corresponding to 60 W power supply, as shown in Table 2. FIGS. 5*a–f* show a comparison of particle size distribution of lysozyme particles obtained in each of these experiments. FIG. 6 is an SEM micrograph of the unprocessed lysozyme sample as obtained from the manufacturer. Comparison of FIGS. 4*a–f* and 6 clearly illustrate the change in morphology and the size of the particles due to SAS-EM processing. FIG. 7 shows the relationship between average particle size and the input power corresponding to different vibration amplitudes. These experiments show that both the volume-average particle size ($S_{vol}$) and the number-average particle size ($S_{num}$) decreases with increasing input power to the vibration source (A) according to following equations 1–2

$$S_{vol}=0.0002A^2-0.0358A+1.7448 \quad (1)$$

$$S_{num}=0.0001A^2-0.0211A+1.1137 \quad (2)$$

Hence, one can use the input power/amplitude of vibration to tune the apparatus that gives desired particle size.

It is interesting to see that the particle size decreases to a minimum value for input power of 90 W. Further increase in the power does not change particle size significantly.

Apart from a decrease in the particle size there is also a considerable decrease in the standard deviation with increasing power as shown in FIG. 8. This is due to the narrow droplet size distribution obtained in the SAS-EM technique, which leads to the formation of uniform sized particles.

The vibration is helping favorably in terms of decreasing the particle size. But for biological molecules, it is also important that no other chemical changes are caused that may reduce the activity of the substance. Hence, experiments were also conducted to check the biological activity of the protein particles that were exposed to vibration during their formation.

A bacterial suspension was prepared by mixing 20 mg of micrococcus lysodeikticus with 90 ml of phosphate buffer (pH=7) and 10 ml of 1% NaCl solution. Lysozyme solution of concentration 0.04 mg/ml was also prepared in the phosphate buffer (pH=7). Now, 0.25 ml of the protein solution was added to 2.5 ml of the bacterial suspension and mixed. The biological activity of lysozyme was determined by measuring the rate of change in ultraviolet (UV) absorbance at 450 nm using a spectrophotometer (Spectronic Genesys-2). The results of the experiments have been shown in FIG. 9. The rate of absorbance is linear for 4 minutes and is proportional to the concentration of the biologically active lysozyme. Based on these results it can be concluded that lysozyme particles obtained from the SAS-EM technique at vibration amplitude corresponding to 60 W power supply, retained 87±5% of their activity. Hence there appears to be no significant loss in the enzymatic activity of the particles obtained from the SAS-EM technique.

(2) Formation of Tetracycline Particles

The SAS-EM technique was carried out at different amplitude of vibration of the horn surface 13 to produce tetracycline particles of different sizes. The particle production vessel was kept constant at 96.5 bar and 35° C. while the vibration frequency of the horn was maintained at 20 kHz. The solution containing tetracycline in tetra hydrofuran (THF, concentration 5 mg/ml) was then introduced into the vessel at different horn amplitudes corresponding to 0–120 watt input power. FIGS. 10*a*1–*d*2 are SEM micrographs of particles obtained from experiments conducted at the different horn amplitudes. With no vibration i.e. when the input power was zero tetracycline fibers around 2 μm in diameter were obtained. A few particles having a mean size of 800 nm were also obtained but most of the solids were in the form of a fine mesh of fibers having a low mechanical strength as shown in FIGS. 11*a–d*. It is important to note here that the experiment conducted at zero amplitude was similar to the conventional SAS. The nozzle was placed parallel to the horn surface 13 without touching the horn for SAS experiments. In SAS-EM experiments, nozzle is placed at angle to the horn surface 13 (0–90°) to maximize the solution jet exposure to the horn surface 13. As the power supply to the horn was increased there was a considerable decrease in the size of the particles obtained as shown in Table 3. FIGS. 12*a–d* show a comparison of particle size distribution of tetracycline particles obtained from experiments conducted at different horn vibration amplitudes.

Vibration Intensity (Input Power Supply) for Controlling Particle Size

From the results in Table 3 it is interesting to note that with an increase in the power supply (i.e., increase in the horn vibration amplitude), there is a considerable decrease in the particle size. As low as 100 nm size particles are obtained at 120 W power supply. FIG. 13 showing the relationship between average particle size and power to the horn, clearly illustrates the trend. The volume average ($S_{vol}$) and number average ($S_{num}$) particle sizes are related to the input power (P) as $$S_{vol}=-0.0016P^3+0.3644P^2-26.461P+795.8 \quad (1)$$

$$S_{num}=-0.0018P^3+0.4298P^2-34.141P+1097.1 \quad (2)$$

where, $S_{vol}$ and $S_{num}$ are in nm and P is in Watts.

Apart from a decrease in the particle size there is also a considerable decrease in the standard deviation in the particle size at higher horn vibration amplitudes as shown in FIG. 14. This is due to the narrow droplet size distribution obtained in the SAS-EM technique, which leads to the formation of more uniform sized particles.

Fourier Transform Infrared Spectroscopy (FTIR) Analysis of Tetracycline Nanoparticles FT-IR analysis was performed to check if there is any difference in the structures of the original tetracycline (as supplied by the manufacturer) and that obtained from the precipitation experiments using the SAS-EM technique at 120 W power supply. FIG. 15 shows the IR spectra obtained in both the cases. Comparison of the two spectra show that there is no variation in the molecular structure of the two tetracyclines. In the case of tetracycline, the carbonyl region between 1500–1600 $cm^{-1}$ and the amide region between 3000–4000 $cm^{-1}$ are of greatest importance to chemists. These regions seem to be similar in case of both the original and the SAS-EM precipitated tetracycline samples confirming that no structural changes took place in the SAS-EM process.

(3) Formation of Griseofulvin (GF) Nanoparticles

The SAS-EM technique was used to produce Griseofulvin particles of different sizes. The results of the different precipitation runs have been summarized in Table 4. Precipitation of GF was carried out using two different solvents, dichloromethane (DCM) and Tetrahydrofuran (THF). All SAS-EM particle production experiments were carried out at 96.5 bar and at 35° C. The vibration frequency of the horn surface 13 was kept constant at 20 KHz while the amplitude of vibration was varied by changing the input power supply to vibrating source. The concentration of the GF solution used during the precipitation experiment was 5 mg/ml of the solvent. FIGS. 16*a–f* and 18*a–e* are SEM micrographs of particles obtained from experiments conducted at the different horn amplitudes using DCM and THF as solvents respectively.

When DCM was used as the solvent and when there was no power supply to the transducer, long needle shaped crystals of several millimeters in length were obtained (FIG. 16*a*). It is important to note here that experiments conducted with no vibration were basically the SAS process. Results obtained in these cases were similar to the ones obtained by Reverchon et al. (1999) during their SAS experiments. In experiments using SAS-EM, nozzle was placed at angle to the horn surface 13 (0–90°) to maximize the solution jet exposure to the horn surface 13. As the power supply to the vibration source was increased, mixtures of long needle shaped crystals of GF and small spherical shaped GF nanoparticles were obtained. FIGS. 17*a–d* are SEM micrographs of the spherical shaped GF nanoparticles obtained from each of these experiments corresponding to different values of input power. When the total power supply was 90 W, narrower and shorter needle shaped crystals of GF were obtained (FIG. 16*c*). A low yield of spherical shaped GF particles were also obtained, but most of the solid was in the form of long needle shaped crystals 50 μm long and 2.5 μm wide.

As the power supply to the transducer was increased, a drastic change in the morphology of the particles was observed. Relatively a small amount of long needle shaped GF crystals were obtained when the total power supply to the transducer was 120 W. The volumetric mean of the spherical GF nanoparticles obtained in this case was 0.13 μm (FIG. 17*b*) while the larger needle like GF crystals were 7.3 μm long and 2.7 μm wide (FIG. 16*d*). Increase in the power supply beyond 120 W further increased the yield of spherical shaped GF nanoparticles. The volumetric mean of the spherical GF particles obtained corresponding to 150 W total power supply was 0.5 μm (FIG. 17*c*) while the larger needle like GF crystals were 3.8 μm long and 1.4 μm wide (FIG. 15*e*). At 180 W power supply the volumetric mean of the spherical shaped GF nanoparticles was 0.4 μm (FIG. 17*d*). A low yield of large GF particles 2.0 μm long and 1.6 μm wide were also obtained (FIG. 16*f*).

When THF was used as the solvent, with no power supply to the transducer, long fibers of GF were obtained (FIG. 18*a*). When the total power supply was increased to 90 W, there was a change in the morphology of the particles and long needle shaped crystals of GF 45 μm long and 2.5 μm wide were obtained (FIG. 18*b*). As the power supply was further increased to 120 W, there was again a change in the morphology of the particles and a mixture spherical and long needle shaped particles of GF were obtained. FIGS. 19*a–c* are SEM micrographs of spherical shaped GF nanoparticles obtained from each of these experiments corresponding to different values of total power supply. The volumetric mean size of the spherical shaped nanoparticles was 0.2 μm (FIG. 19*a*) while the mean size of the needle shaped GF crystals was 8.0 μm long and 1.0 μm wide (FIG. 18*c*). The volumetric mean of the spherical GF particles when the power supply was 150 W was 0.3 μm (FIG. 19*b*) while the mean size of the needle shaped GF crystals was 3.8 μm long and 1.6 μm wide (FIG. 18*d*). At 180 W power supply, spherical GF particles having a volumetric mean size of the 0.2 μm (FIG. 19*c*) were obtained. Very few larger needle shaped GF particles 2.1 μm long and 1.7 μm wide were also obtained (FIG. 18*e*).

Effect of Vibration Intensity on Size and Morphology of Griseofulvin Nanoparticles From the above results it is interesting to note that, with an increase in power supply (i.e. increase in horn vibration amplitude) there is an increase in the yield of small spherical Griseofulvin nanoparticles. Further, there is also a decrease in the size and the yield of the larger needle shaped Griseofulvin crystals obtained. This has been illustrated in FIGS. 16*a–f,* 18*a–e* and 20 where upon visual inspection one can see a change in morphology of the particles with increased power supply and also a decrease in the yield of large needle shaped Griseofulvin crystals. FIG. 21 is a graph showing the relationship between the mean size of the spherical particles and the input power supply corresponding to different horn vibration amplitudes. From the figure one can infer that Griseofulvin nanoparticles having a volumetric mean as low as 130 nm have been obtained corresponding to 120 W power supply and when DCM was used as the solvent. FIG. 22 is a graph showing the relationship between the volume of the large needle shaped Griseofulvin crystals and input power supply. There is a considerable decrease in the volume of Griseofulvin crystals with increasing power supply in case of both the solvents. Based on the FIGS. 21 and 22, no particular trend can be established about the effect of the solvent on the size and morphology of Griseofulvin particles.

(4) Formation of Fullerene Particles

In order to demonstrate the effectiveness of the current invention for processing other materials besides pharmaceutical substances, the SAS-EM technique was applied for the precipitation of fullerene $C_{60}$ nanoparticles. In this case, the particle production vessel was kept constant at 96.5 bar and 37° C. and the frequency of the horn vibrations was maintained at 20 kHz. A solution of fullerene in toluene (concentration, 0.6 mg/ml) was used for all the precipitation experiments. The first experiment, as in all the earlier cases, was performed with no vibration and was similar to the SAS technique for precipitation of particles. The particles obtained by this technique were 96 nm in size with standard deviations of around 43 nm.

Next, the particle production experiment was performed with the vibrating horn surface 13 inside the vessel and input power set at 30 W power. The 75 μm capillary tube in this case was placed parallel to the horn surface 13 touching it completely. Particles formed in this case were extremely small having a mean diameter of 30 nm and a standard deviation of 13 nm.

(5) Formation of Polymer Encapsulated or Coated Magnetite Particles

The use of SAS-EM technique was also demonstrated for the encapsulation or coating of core particles by one or more compounds to form composite nanoparticles. Similar to earlier examples, SAS-EM precipitation experiments were carried out at 96.5 bar and at 35° C. The vibration frequency of the horn surface 13 was kept constant at 20 KHz while the amplitude of vibration was varied by changing the total power supply to the vibration source. A sample of commercial magnetite particles (Ferrofluid) was obtained that had magnetite particles (10 nm) suspended in a hydrocarbon mineral oil using a fatty acid surfactant. The solution for injection into the particle production vessel was prepared by dissolving the polymer (poly(lactide-co-glycolide)(PLGA), 100 mg) and the above ferrofluid (49 mg) in 10 ml of dicholoromethane (DCM).

When there was no vibration (i.e similar to a SAS experiments) PLGA encapsulated magnetite particles having a mean size of 1.7 μm were obtained as shown in FIG. 23*a*. FIG. 24 is a TEM micrograph of the obtained composite particles clearly showing the magnetite particles encapsulated in the polymer matrix. When the power supply to the vibration source was increased to 60 W. there was a reduction in mean particle size to 0.7 μm as shown in FIG. 23*b*. With increase in the power supply there is a further reduction in mean particle size to as much as 0.4 μm as shown in FIG. 23*c*.

(6) Formation of Tetracycline Particles Using a Higher Diameter Nozzle

In all the previous experiments a 75 μm silica capillary tube was used to spray the solution having at least one substance of interest and in at least one solvent onto or near the horn surface. In the present experiments we have used a nozzle having a higher diameter in order to study the effect of increase in nozzle diameter on the size and the morphology of the particles.

Like the earlier experiments here the SAS-EM technique was carried out at different amplitude of vibration of the vibrating horn surface to produce tetracycline particles of different sizes and morphologies. The diameter of the stainless steel capillary used in this case however was a 760 μm. The precipitation cell in this case was kept constant at 96.5 bar and 35° C. while the frequency of the titanium horn was maintained at 20 kHz. The solution jet was then introduced into the cell at different horn amplitudes corresponding to 0–120 W power supplied. FIGS. 25*a–f* are SEM micrographs of particles obtained from these experiments. With no vibration i.e. when the horn amplitude was zero, tetracycline fibers around 1–2 μm in thick were obtained. Most of the solid was in the form of this fine mesh of fibers having a low mechanical strength as shown in FIGS. 25*a, b*. It is important to note here that the experiment conducted at zero amplitude was similar to the conventional SAS. The nozzle was placed parallel to the horn surface without touching the horn for SAS experiments. As the power supply to the horn was increased there was a drastic change in the morphology of the particles. When the power supply was 60 W flaky crystals of tetracycline about 5.0 μm long and 1.0 μm wide were obtained as shown in FIGS. 25*c, d*. Further increase in the power supply again resulted in a drastic change in morphology of the particles. Fine nanoparticles of tetracycline having a volumetric mean diameter of 0.28 μm and a standard deviation of 0.13 μm were obtained when the power supply was 120 W (FIGS. 25*e, f*)

We claim:

1. A method for a manufacture of particles of a desired substance comprising:

(a) vibrating a surface at a desired frequency;

(b) applying a dispersion having at least a solvent and the desired substance on to or close to the vibrating surface to generate droplets; and (c) applying an antisolvent at near or supercritical conditions to the droplets which results in the desired substance in the form of particles, the solvent being miscible with the antisolvent and the desired substance being substantially insoluble in the antisolvent.

2. The method as recited in claim 1 including changing the size of the particles by changing intensity of vibration of the surface.

3. The method as recited in claim 1 including changing the distribution of the particles by changing intensity of vibration of the surface.

4. The method as recited in claim 1 wherein the vibration of the surface is by a piezoelectric means.

5. The method as recited in claim 1 wherein the vibration of the surface is by a magnetorestrictive means.

6. The method as recited in claim 1 including reducing agglomeration of the particles by changing the intensity of vibrations of the surface.

7. The method as recited in claim 1 including collecting the particles in a continuous manner.

8. The method as recited in claim 1 wherein the dispersion containing said desired substance is applied continuously.

9. The method as recited in claim 1 wherein the antisolvent being selected from the group consisting of carbon dioxide, propane, butane, isobutane, nitrous oxide, sulfur hexafluoride and trifluoromethane or a combination thereof.

10. The method as recited in claim 1 wherein the desired substance are medicaments.

11. The method as recited in claim 1 including:

(i) measuring the particle size; and (ii) changing the particle size by changing the intensity of the vibrations of the surface.

12. The method as recited in claim 1 including changing the morphology of the particle by changing intensity of vibration of the surface.

13. A method for making encapsulated coreparticles with a desired substance comprising:

(a) vibrating a surface at a desired frequency;

(b) applying a dispersion having at least a solvent, coreparticles and the desired substance on to or close to the vibrating surface; and (c) applying an antisolvent at near or supercritical conditions to the dispersion which results in the desired substance encapsulating the coreparticles, the solvent being miscible with the antisolvent and the desired substance being substantially insoluble in the antisolvent.

14. The method as recited in claim 13 including changing the size of the encapsulated coreparticles by changing intensity of vibration of the surface.

15. The method as recited in claim 13 including changing the distribution of the encapsulated coreparticles by changing intensity of vibration of the surface.

16. The method as recited in claim 13 wherein the vibration of the surface is by a piezoelectric means.

17. The method as recited in claim 13 wherein the vibration of the surface is by a magnetorestrictive means.

18. The method as recited in claim 13 including reducing agglomeration of the encapsulated coreparticles by changing the intensity of vibrations of the surface.

19. The method as recited in claim 13 including collecting the encapsulated coreparticles in a continuous manner.

20. The method as recited in claim 13 wherein the dispersion is applied continuously.

21. The method as recited in claim 13 wherein the antisolvent being selected from the group consisting of carbon dioxide, propane, butane, isobutane, nitrous oxide, sulfur hexafluoride and trifluoromethane or a combination thereof.

22. The method as recited in claim 13 wherein the desired substance are medicaments.

23. The method as recited in claim 13 including:

(i) measuring the encapsulated coreparticle size; and (ii) changing the encapsulated coreparticle size by changing the intensity of the vibrations of the surface.

24. A method for a manufacture of particles of a desired substance comprising:

(a) vibrating a surface at a desired frequency;

(b) applying a dispersion having at least a solvent and the desired substance on the vibrating surface to generate droplets; and (c) applying an antisolvent at near or supercritical conditions to the droplets which results in the desired substance in the form of particles, the solvent being miscible with the antisolvent and the desired substance being substantially insoluble in the antisolvent.

25. The method as recited in claim 24 including changing the size of the particles by changing intensity of vibration of the surface.

26. The method as recited in claim 24 including changing the distribution of the particles by changing intensity of vibration of the surface.

27. The method as recited in claim 24 wherein the vibration of the surface is by a piezoelectric means.

28. The method as recited in claim 24 wherein the vibration of the surface is by a magnetorestrictive means.

29. The method as recited in claim 1 including reducing agglomeration of the particles by changing the intensity of vibrations of the surface.

* * * * *

UNITED STATES PATENT AND TRADEMARK OFFICE

CERTIFICATE OF CORRECTION

PATENT NO. : 6,620,351 B2
DATED : September 16, 2001
INVENTOR(S) : Ram B. Gupta and Pratibhash Chattopadhyay It is certified that error appears in the above-identified patent and that said Letters Patent is hereby corrected as shown below:

<u>Title page,</u>
"25 Drawing Sheets" should read -- 26 Drawing Sheets --.

<u>Drawings,</u>
"10-25" should be renumbered as -- 11-26 --.

Insert attached image between Sheet 9 and 25 and Sheet 10 of 25.

Signed and Sealed this

Second Day of March, 2004

JON W. DUDAS
*Acting Director of the United States Patent and Trademark Office*

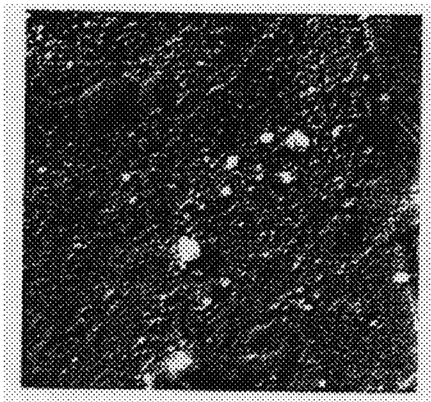
(a1) x 5000
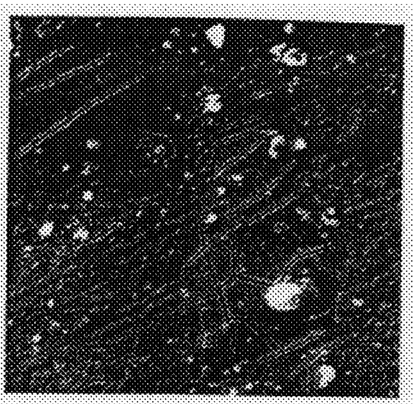
(a2) x 5000
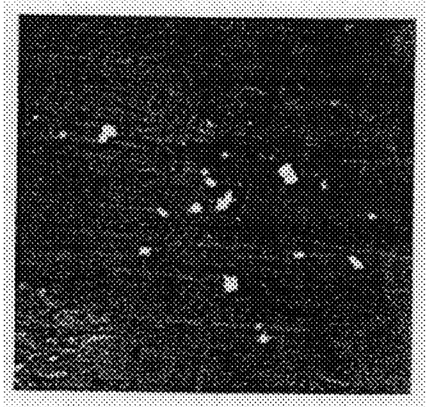
(b1) x 10,000
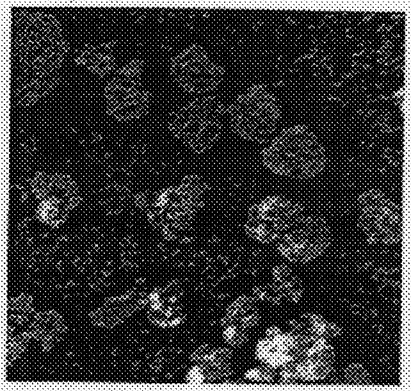
(b2) x 5000
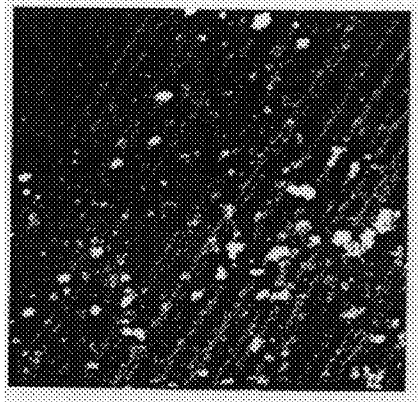
(c1) x 10,000
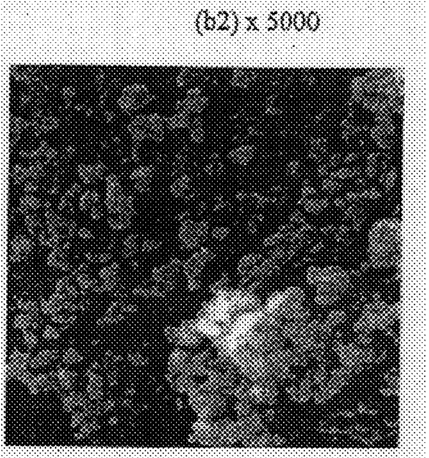
(c2) x 20,000